United States Patent
Lu et al.

(10) Patent No.: US 10,350,305 B2
(45) Date of Patent: Jul. 16, 2019

(54) COMPOSITIONS FOR TREATING DYSTROGLYCANOPATHY DISORDERS

(71) Applicants: THE CHARLOTTE-MECKLENBURG HOSPITAL AUTHORITY, Charlotte, NC (US); THE UNIVERSITY OF NORTH CAROLINA AT CHAPEL HILL, Chapel Hill, NC (US)

(72) Inventors: Qi Long Lu, Charlotte, NC (US); Xiao Xiao, Chapel Hill, NC (US)

(73) Assignees: THE UNIVERSITY OF NORTH CAROLINA AT CHAPEL HILL, Chapel Hill, NC (US); THE CHARLOTTE MECKLENBURG HOSPITAL AUTHORITY, Charlotte, NC (US)

( * ) Notice: Subject to any disclaimer, the term of this patent is extended or adjusted under 35 U.S.C. 154(b) by 0 days.

(21) Appl. No.: 15/687,196

(22) Filed: Aug. 25, 2017

(65) Prior Publication Data

US 2017/0368199 A1 Dec. 28, 2017

Related U.S. Application Data

(63) Continuation of application No. PCT/US2016/019783, filed on Feb. 26, 2016.

(60) Provisional application No. 62/126,271, filed on Feb. 27, 2015.

(51) Int. Cl.
| | |
|---|---|
| *A61K 48/00* | (2006.01) |
| *C07K 14/47* | (2006.01) |
| *A61K 38/17* | (2006.01) |
| *C12N 15/86* | (2006.01) |
| *C12N 9/10* | (2006.01) |
| *A01K 67/027* | (2006.01) |
| *A61K 38/00* | (2006.01) |

(52) U.S. Cl.
CPC ...... *A61K 48/0058* (2013.01); *A01K 67/0275* (2013.01); *A61K 38/1719* (2013.01); *C07K 14/4707* (2013.01); *C12N 9/10* (2013.01); *C12N 15/86* (2013.01); *A01K 2217/052* (2013.01); *A01K 2227/105* (2013.01); *A61K 38/00* (2013.01); *C12N 2750/14143* (2013.01); *C12N 2800/22* (2013.01); *C12N 2830/008* (2013.01)

(58) Field of Classification Search
CPC ........... A61K 48/0058; A61K 38/1719; C07K 14/4707; C12N 15/86; A01K 2217/052
See application file for complete search history.

(56) References Cited

FOREIGN PATENT DOCUMENTS

WO 2013/151665 10/2013

OTHER PUBLICATIONS

Xu et al Molecular Ther. 21, 10, 1832-1840, IDS (Year: 2013).*
Genbacnk accession No. AJ314847.1, pp. 1 (Year: 2008).*
Kim et al Gene 199 , 293-301 (Year: 1997).*
Qiao et al Gene Ther. April ; 18(4): 403-410 (Year: 2011).*
Rychlik et al. Nuc. Acids Res. 18:6409-6412 (Year: 1990).*
NCBI accession No. JV628506.1, 2014, pp. 1-2 (Year: 2014).*
Vannoy et al Human Gene Therapy Methods, 25, 187-196 (Year: 2014).*
Kaiser Science, 317, 580 (Year: 2007).*
Verma—Annu Rev Biochem. 74:711-38 (Year: 2005).*
Thomas et al. Nature Rev.Genet. 4: 346-358 (Year: 2003).*
Brockstedt et al Clinical Immunol. 92:67-75 (Year: 1999).*
Vannoy et al Molecular Therapy, 5, 31-42 (Year: 2017).*
McTiernan et al Gene Therapy, 14, 1613-1622 (Year: 2007).*
Donahue et al, Proc. Natl Acad Sci US A. 94: 4664-4668 (Year: 1997).*
Holschneider et al. Int J Devl Neuroscience, 18: 615-618 (Year: 2000).*
International Preliminary Report on Patentability and Written Opinion corresponding to International Application No. PCT/US2016/019783, dated Aug. 29, 2017, 5 pages.
Xu, Lei et al. "Adeno-associated Virus 9 Mediated FKRP Gene Therapy Restores Functional Glycosylation of Dystroglycan and Improves Muscle Functions", *The American Society of Genes & Cell Therapy*, vol. 21, No. 10, 16 pages (Oct. 2013).
GenBankAJ314847 *Homo sapiens* mRNA for fukutin-related protein (FKRP gene), 2 pages (2008).
Blaeser, A. et al. "Mouse models of fukutin-related protein mutations show a wide range of disease phenotypes", *Hum Genet*, 12 pages (2013).
Kudla, G. et al. "High guanine and cytosine content increases mRNA levels in mammalian cells", PLOS Biology, vol. 4, issue 6, 10 pages (2016).
Extended European Search Report corresponding to European application No. 16756450.9, dated Jun. 28, 2018, 9 pages.

* cited by examiner

*Primary Examiner* — Anoop K Singh
(74) *Attorney, Agent, or Firm* — Myers Bigel, P.A.

(57) ABSTRACT

The invention relates to synthetic polynucleotides encoding fukutin related protein (FKRP). The invention further relates to nucleic acid constructs comprising the synthetic polynucleotides and methods of using these synthetic polynucleotides to treat dystroglycanopathy disorders.

11 Claims, 3 Drawing Sheets

Specification includes a Sequence Listing.

SEQUENCE LISTING

<160> NUMBER OF SEQ ID NOS: 2

<210> SEQ ID NO 1
<211> LENGTH: 1488
<212> TYPE: DNA
<213> ORGANISM: Artificial
<220> FEATURE:
<223> OTHER INFORMATION: Optimized nucleotide coding sequence for FKRP

<400> SEQUENCE: 1

```
atgagactga caagatgcca ggccgccctg ccgctgcca tcacactgaa tctgctggtg      60
ctgttctatg tgtcctggct gcagcaccag ccccggaact ctagagccag aggcccaaga    120
agggcctctg ccgccggacc tagagtgaca gtgctcgtgc gcgagttcga ggccttcgac    180
aatgccgtgc ccgagctggt ggacagcttc ctgcagcaag accctgctca gcctgtggtg    240
gtggccgccg atacactgcc ttatcctcca ctggccctgc ccagaatccc caatgtcgca    300
```

| | |
|---|---|
| ctggctctgc tgcagcccgc cctggataga cctgccgccg ctagcagacc tgagacatac | 360 |
| gtggccaccg agttcgtggc cctggtgcct gatggcgcca gagctgaagc tcccggcctg | 420 |
| ctggaaagaa tggtggaagc cctgagagcc ggcagcgcca gactggtggc tgctcctgtg | 480 |
| gctaccgcca accctgccag atgtctggcc ctgaatgtgt ccctgagaga gtggaccgcc | 540 |
| agatacggcg ctgcccctgc cgctcctaga tgtgatgctc tggatggcga cgccgtggtg | 600 |
| ctgctgagag ccagggacct gttcaacctg agcgcccctc tggccagacc tgtgggcaca | 660 |
| agcctgtttc tgcagacagc cctgaggggc tgggccgtgc agctgctgga tctgacattt | 720 |
| gccgctgcca gacagcctcc tctggccaca gccatgccag atggaaggc cgagagagag | 780 |
| ggcagagcca aagggctgc tctgctgagg gccctgggca tcagactggt gtcttgggaa | 840 |
| ggcggcagac tcgagtggtt cggctgcaac aaagaaacca cccggtgctt cggcaccgtc | 900 |
| gtgggcgata caccagccta cctgtacgag aaagatgga ccccccttg ctgcctgcgg | 960 |
| gccctgagag aaacagccag atatgtcgtg ggcgtgctgg aagccgctgg cgtgcgatat | 1020 |
| tggctggaag gcggatctct gctgggagcc gccaggcacg cgacatcat ccttgggac | 1080 |
| tacgacgtgg acctgggcat ctacctggaa gatgtgggca actgcgagca gctgagaggc | 1140 |
| gccgaagccg gctctgtggt ggatgagagg ggcttcgtgt gggagaaggc cgtggaaggc | 1200 |
| gacttcttcc gggtgcagta cagcgagagc aaccatctgc atgtggacct gtggcccttc | 1260 |
| taccccgga acggcgtgat gaccaaggac acctggctgg accaccggca ggacgtggaa | 1320 |
| ttccccgagc actttctgca gcccctggtg ccactgcctt cgccggatt tgtggcccag | 1380 |
| gcccccaaca actaccggcg gttcctgaa ctgaagttcg ccctggcgt gatcgagaac | 1440 |
| ccccagtacc ctaaccctgc cctgctgagc ctgaccggca gcggctaa | 1488 |

<210> SEQ ID NO 2
<211> LENGTH: 1488
<212> TYPE: DNA
<213> ORGANISM: Homo sapiens

<400> SEQUENCE: 2

| | |
|---|---|
| atgcggctca cccgctgcca ggctgccctg gcggccgcca tcaccctcaa ccttctggtc | 60 |
| ctcttctatg tctcgtggct gcagcaccag cctaggaatt cccgggcccg ggggccccgt | 120 |
| cgtgcctctg ctgccggccc ccgtgtcacc gtcctggtgc gggagttcga ggcatttgac | 180 |
| aacgcggtgc ccgagctggt agactccttc ctgcagcaag acccagccca gcccgtggtg | 240 |
| gtggcagccg acacgctccc ctacccgccc tggccctgc ccgcatccc caacgtgcgt | 300 |
| ctggcgctgc tccagcccgc cctggaccgg ccagccgcag cctcgcgccc ggagacctac | 360 |
| gtggccaccg agtttgtggc cctagtacct gatgggcgc gggctgaggc acctggcctg | 420 |
| ctggagcgca tggtggaggc gctccgcgca ggaagcgcac gtctggtggc cgccccggtt | 480 |
| gccacggcca accctgccag gtgcctggcc ctgaacgtca gcctgcgaga gtggaccgcc | 540 |
| cgctatggcg cagcccccgc cgcgccccgc tgcgacgccc tggacggaga tgctgtggtg | 600 |
| ctcctgcgcg cccgcgacct cttcaacctc tcggcgcccc tggccggcc ggtgggcacc | 660 |
| agcctctttc tgcagaccgc ccttcgcggc tgggcggtgc agctgctgga cttgaccttc | 720 |
| gccgcggcgc gccagccccc gctggccacg gcccacgcgc gctggaaggc tgagcgcgag | 780 |
| ggacgcgctc ggcggggcgg cgctgctccg cgctgggca tccgcctagt gagctgggaa | 840 |
| ggcgggcggc tggagtggtt cggctgcaac aaggagacca cgcgctgctt cggaaccgtg | 900 |
| gtgggcgaca cgcccgccta cctctacgag gagcgctgga cgcccccctg ctgcctgcgc | 960 |

-continued

```
gcgctgcgcg agaccgcccg ctatgtggtg ggcgtgctgg aggctgcggg cgtgcgctac    1020
tggctcgagg gcggctcact gctggggggcc gcccgccacg gggacatcat cccatgggac    1080
tacgacgtgg acctgggcat ctacttggag gacgtgggca actgcgagca gctgcggggg    1140
gcagaggccg gctcggtggt ggatgagcgc ggcttcgtat gggagaaggc ggtcgagggc    1200
gactttttcc gcgtgcagta cagcgaaagc aaccacttgc acgtggacct gtggcccttc    1260
tacccccgca atggcgtcat gaccaaggac acgtggctgg accaccggca ggatgtggag    1320
tttcccgagc acttcctgca gccgctggtg cccctgccct ttgccggctt cgtggcgcag    1380
gcgcctaaca actaccgccg cttcctggag ctcaagttcg ggcccggggt catcgagaac    1440
ccccagtacc ccaacccggc actgctgagt ctgacgggaa gcggctga              1488
```

COMPOSITIONS FOR TREATING DYSTROGLYCANOPATHY DISORDERS

PRIORITY

This application is a continuation application of International Application Serial No. PCT/US2016/019783, filed Feb. 26, 2016, which claims the benefit, under 35 U.S.C. § 119 (e), of U.S. Provisional Application No. 62/126,271 was filed on Feb. 27, 2015, the entire contents of each of which are incorporated by reference herein.

STATEMENT OF FEDERAL SUPPORT

This invention was made with government support under Grant No. 1R01NS082536-01 and Grant No. NS082536 awarded by the National Institutes of Health. The government has certain rights in this invention.

STATEMENT REGARDING ELECTRONIC FILING OF A SEQUENCE LISTING

A Sequence Listing in ASCII text format, submitted under 37 C.F.R. § 1.821, entitled 1184-9_ST25.txt, 4583 bytes in size, generated Aug. 25, 2017 and filed via EFS-Web, is provided in lieu of a paper copy. This Sequence Listing is hereby incorporated herein by reference into the specification for its disclosures.

FIELD OF THE INVENTION

The invention relates to synthetic (optimized or not naturally Occurring) polynucleotides encoding fukutin related protein (FKRP). The invention further relates to nucleic acid constructs comprising the synthetic polynucleotides and methods of using these polynucleotides to treat dystroglycanopathy disorders (e.g., that involve a reduction in glycoslation of alpha-dystroglycan ($\alpha$-DG).

BACKGROUND OF THE INVENTION

Muscular dystrophies (MDs) are a class of hereditary, degenerative disorders of striated muscles caused by defects in genes that encode a diverse group of proteins. Dystroglycanopathies are a particular subset of MDs that share the same biochemical feature of reduced glycosylation of $\alpha$-dystroglycan and diminished laminin binding activity. Dystroglycanopathies are the second most commonly occurring group of MDs, second only to Duchenne muscular dystrophy. The different disorders within dystroglycanopathies show a wide spectrum of clinical severities. (Qiao et al. *Molecular Therapy* doi:10.1038/mt.2014.141; pp 1-10 (Jul. 22, 2014); Blaeser et al. *Hum Genet* 132:923-934 (2013).

Dystroglycan (DG) consists of a heavily glycosylated extracellular $\alpha$ subunit ($\alpha$-DG) and a transmembrane $\beta$ subunit ($\beta$-DG). $\alpha$-DG and $\beta$-DG are encoded by a single gene and are post translationally cleaved to generate the two subunits. $\alpha$-DG is a cell surface receptor for several extracellular matrix proteins including laminin, agrin, and perlecan in muscle, and neurexin in the brain. DG functions as a molecular anchor, connecting the extracellular matrix with the cytoskeleton across the plasma membrane in skeletal muscle. Deficiencies in $\alpha$-DG post-translational modification is largely responsible for the disorders that make up the dystroglycanopathies. One of the proteins identified to be in the DG glycosylation pathway is fukutin-related protein (FKRP), which is involved in the glycosylation of O-linked mannose in $\alpha$-DG (Qiao et al. *Molecular Therapy* doi: 10.1038/mt.2014.141 pp 1-10 (Jul. 22, 2014); Blaeser et al. *Hum Genet* 132:923-934 (2013)).

Mutations in the gene encoding FKRP result in a wide spectrum of disease phenotypes including the mild limb-girdle muscular dystrophy 2I (LGMD2I), the severe Walker-Warburg syndrome, and muscle-eye-brain disease. Currently, no effective treatment is known for dystroglycanopathies involving a reduction in glycoslation of $\alpha$-DG (Xu et al. *Mol. Therapy* 21:10doi:10.1038/mt.2013.156 (Jul. 2, 2013)).

The present invention overcomes previous shortcomings in the art by providing methods and compositions to treat dystroglycanopathies associated with a deficiency in reduction in glycoslation of $\alpha$-DG.

SUMMARY OF THE INVENTION

The present invention is based in part on the surprising finding that a reduction in GC content of the nucleotide sequence encoding the fukutin-related protein (FKRP) increases expression of FKRP. Accordingly, in one aspect, the invention provides a synthetic polynucleotide encoding a human FKRP, wherein the synthetic polynucleotide comprises the nucleotide sequence of SEQ ID NO:1; and/or a nucleotide sequence having at least 90% identity to SEQ ID NO:1; and/or a synthetic polynucleotide comprising a nucleotide sequence encoding FKRP, wherein the GC content is reduced by about 5% to about 10% compared to the GC content of SEQ ID NO:2.

In another aspect, the synthetic polynucleotide is operably linked to a promoter.

In a further aspect, the invention provides a vector comprising the synthetic polynucleotide of the invention. In some aspects the vector is a viral vector. In particular aspects, the vector is an adeno-associated virus (AAV) vector.

In an additional aspect, the invention provides a transformed cell comprising the synthetic polynucleotide of the invention and/or a vector comprising the synthetic polynucleotide of the invention. In some aspects, the invention provides a transgenic animal comprising the synthetic polynucleotide, the vector, and/or the transformed cell of the invention.

In still further aspects, the invention provides a method of increasing glycosylation of alpha-dystroglycan ($\alpha$-DG) in a cell, comprising: delivering to said cell the synthetic polynucleotide of the invention and/or a vector comprising the synthetic polynucleotide of the invention, wherein the synthetic polynucleotide is expressed in said cell, thereby producing FKRP and increasing glycosylation of $\alpha$-DG.

In other aspects, the invention provides a method of delivering a nucleic acid to a cell is provided, the method comprising delivering to the cell a synthetic polynucleotide of the invention, and/or a vector and/or a transformed cell comprising a synthetic polynucleotide of the invention. In some embodiments, the synthetic polynucleotide of the invention, and/or vector and/or transformed cell may be delivered to the subject in a therapeutically effective amount.

In still other aspects, a method of delivering a nucleic acid to a subject in need thereof, is provided, the method comprising delivering to the subject a synthetic polynucleotide of the invention, a vector comprising a synthetic polynucleotide of the invention and/or a transformed cell comprising a synthetic polynucleotide of the invention. In some embodiments, the synthetic polynucleotide of the invention, and/or vector and/or transformed cell may be delivered to the subject in a therapeutically effective amount.

In some aspects, a method of treating a dystroglycanopathy in a subject in need thereof, is provided, the method comprising delivering to the subject a therapeutically effective amount of a synthetic polynucleotide of the invention, a vector comprising a synthetic polynucleotide of the invention and/or a transformed cell comprising a synthetic polynucleotide of the invention, thereby treating dystroglycanopathy in the subject. In some aspects of the invention, the dystroglycanopathy comprises a mutation in the nucleic acid encoding FKRP and/or a deficiency in glycosylation of alpha-dystroglycan (α-DG), or any combination thereof. In some aspects of the invention, the dystroglycanopathy is limb girdle muscular dystrophy 2I, congenital muscular dystrophy, Walker-Warburg syndrome, muscle-eye-brain disease, or any combination thereof.

These and other aspects of the invention are set forth in more detail in the description of the invention below.

DETAILED DESCRIPTION OF THE INVENTION

Figure 1:
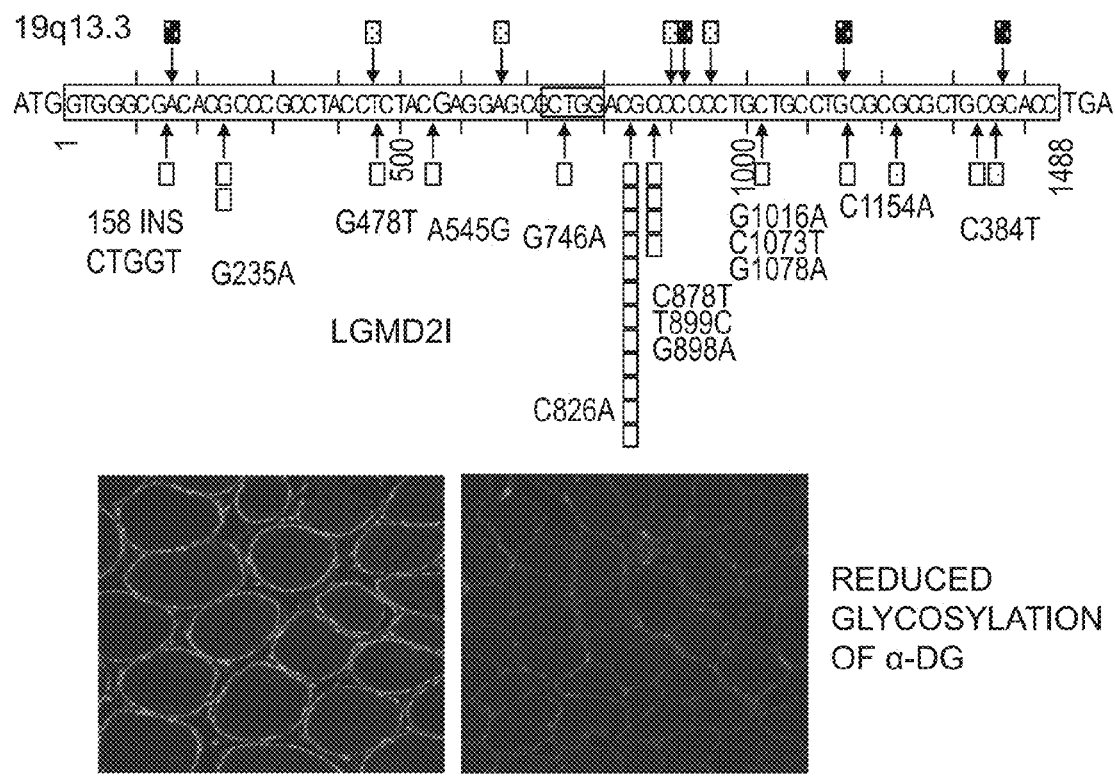
FIG. 1 shows FKRP mutations and reduced glycosylation of α-DG in limb girdle muscular dystrophy 2I (LGMD2I) (lower, right panel) as compared to normal tissue (lower, left panel) using immunofluorescence staining.

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A. B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for cloning genes, amplifying and detecting nucleic acids, and the like. Such techniques are known to those skilled in the art. See, e.g., Sambrook et al., Molecular Cloning: A Laboratory Manual 2nd Ed. (Cold Spring Harbor, N.Y., 1989); Ausubel et al. Current Protocols in Molecular Biology (Green Publishing Associates, Inc. and John Wiley & Sons, Inc., New York).

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of polypeptide, dose, time, temperature, enzymatic activity, GC content and the like, refers to variations of ±20%, ±10%, ±5%, ±1%, ±0.5%, or even ±0.1% of the specified amount.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

The transitional phrase "consisting essentially of" means that the scope of a claim is to be interpreted to encompass the specified materials or steps recited in the claim, "and those that do not materially affect the basic and novel characteristic(s)" of the claimed invention.

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or fewer (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or fewer additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence.

The term "enhance" or "increase" or grammatical variations thereof as used herein refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold or an increase of at least about 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 225%, 250%, 275%, 300%, 400%, 500% or more.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectable activity (at most, an insignificant amount, e.g., less than about 10% or even 5%).

As used herein, "effective amount" refers to an amount of a compound or composition of this invention (e.g., the nucleotide sequence of SEQ NO:1; a nucleotide sequence having at least 90% identity to SEQ ID NO:1; a nucleotide sequence encoding FKRP, wherein the GC content is reduced by about 5% to about 10% compared to the GC content of SEQ ID NO:2 and/or an expression cassette, vector or transgenic cell comprising one or more of the nucleotide sequence of SEQ ID NO:1; a nucleotide sequence having at least 90% identity to SEQ ID NO:1; a nucleotide sequence encoding FKRP, wherein the GC content is reduced by about 5% to about 10% compared to the GC content of SEQ ID NO:2) that is sufficient to produce a desired effect, which can be a therapeutic effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington. *The Science And Practice of Pharmacy* (20th ed. 2000)).

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

The efficacy of treating a dystroglycanopathy by the methods of the invention can be determined by detecting a clinical improvement as indicated by a change in the subject's symptoms and/or clinical parameters as would be well known to one of skill in the art.

By the terms "treat," "treating," or "treatment," it is intended that the severity of the subject's condition is reduced or at least partially improved or modified and that some alleviation, mitigation or decrease in at least one clinical symptom is achieved.

The terms "prevent," "preventing," and "prevention" (and grammatical variations thereof) refer to a decrease or delay in the extent or severity of a disease, disorder and/or clinical symptom(s) after onset relative to what would occur in the absence of carrying out the methods of the invention prior to the onset of the disease, disorder and/or clinical symptom(s). In terms of dystroglycanopathy. "preventing" refers to the occurrence of a increase in glycosylation of alpha-dystroglycan ($\alpha$-DG) as compared to the amount of glycosylation of alpha-dystroglycan ($\alpha$-DG) that occurs in the absence of the therapeutic treatment. Thus, a subject identified to have one or more mutations that are associated with a dystroglycanopathy characterized by reduced glycosylation of $\alpha$-DG can be administered the synthetic/optimized polynucleotides of this invention to prevent/delay/alleviate onset of said dystroglycanopathy. Such mutations are well known in the art.

As used herein, "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides) or produced by cell biology techniques commonly used for vector production. Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid, nucleotide sequence, or polynucleotide of this invention.

An "isolated polynucleotide" is a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid may include some or all of the 5' non-coding (e.g., promoter) sequences that are immediately contiguous to a coding sequence. The term therefore includes, for example, a recombinant DNA/synthetic polynucleotide that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA/synthetic polynucleotide that is part of a hybrid nucleic acid encoding an additional polypeptide or peptide sequence. An isolated polynucleotide that includes a gene is not a fragment of a chromosome that includes such gene, but rather includes the coding region and regulatory regions associated with the gene, but no additional genes naturally found on the chromosome.

The terms "exogenous" and/or "heterologous" as used herein can include a nucleotide sequence that is not naturally occurring in the nucleic acid construct and/or delivery vector (e.g., virus delivery vector) in which it is contained and can also include a nucleotide sequence that is placed into a non-naturally occurring environment and/or position relative to other nucleotide sequences (e.g., by association with a promoter or coding sequence with which it is not naturally associated). A heterologous or exogenous nucleotide sequence or amino acid sequence of this invention can be any heterologous nucleotide sequence and/or amino acid sequence that has been introduced into a cell and can include a nucleotide sequence and/or amino acid sequence for which an original version is already present in the cell and the heterologous nucleotide sequence and/or amino acid sequence is a duplicate of the original naturally occurring version, and/or the heterologous nucleotide sequence or amino acid sequence can be introduced into a cell that does not naturally comprise the same nucleotide sequence and/or amino acid sequence.

The term "synthetic polynucleotide" refers to a polynucleotide sequence that does not exist in nature but instead is made by the hand of man, either chemically, or biologically (i.e., in vitro modified) using cloning and vector propagation techniques.

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated sequences that may be transcribed can be present between a promoter and a nucleotide sequence, and the promoter can still be considered "operably linked" to the nucleotide sequence.

A "promoter" is a nucleotide sequence that controls or regulates the transcription of a nucleotide sequence (i.e., a coding sequence) that is operably associated with the promoter. The coding sequence may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. The promoter region may comprise other elements that act as regulators of gene expression.

The term "fragment," as applied to a polynucleotide, will be understood to mean a nucleotide sequence of reduced length relative to a reference nucleic acid or nucleotide sequence and comprising, consisting essentially of, and/or consisting of a nucleotide sequence of contiguous nucleotides identical or almost identical (e.g., 90%, 92%, 95%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially of, and/or consist of oligonucleotides having a length of at least about 8, 10, 12, 15, 20, 25, 30, 35, 40, 45, 50, 75, 100, 150, 200, or more consecutive nucleotides of a nucleic acid or nucleotide sequence of the invention (e.g., the nucleotide sequence of SEQ ID NO:1; and/or a nucleotide sequence having at least 90% identity to SEQ ID NO:1 and/or a nucleotide sequence encoding FKRP, wherein the GC content is reduced by about 5% to about 10% compared to the GC content of SEQ ID NO:2).

The term "isolated" can refer to a nucleic acid, nucleotide sequence or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence or polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose.

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical or almost identical (e.g., 90%, 92%, 95%, 98%, 99% identical) to the reference polypeptide or amino acid sequence. Such a polypeptide fragment according to the invention may be, where appropriate, included in a larger polypeptide of which it is a constituent, in some embodiments, such fragments can comprise, consist essentially of, and/or consist of peptides having a length of at least about 4, 6, 8, 10, 12, 15, 20, 25, 30, 35, 40, 45, 50, 75, 100, 150, 200, or more consecutive amino acids of a polypeptide or amino acid sequence according to the invention.

The nucleic acid of this invention can be present in a vector and such a vector can be present in a cell. A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in i.e., capable of replication under its own control. Any suitable vector is encompassed in the embodiments of this invention, including, but not limited to, nonviral vectors (e.g., plasmids, liposomes, electrically charged lipids (cytofectins), nucleic acid-protein complexes, poloxymers and biopolymers), viral vectors (e.g., retrovirus, lentivirus, adeno-associated virus, poxvirus, alphavirus, baculovirus, vaccinia virus, herpes virus, Epstein-Barr virus, and adenovirus vectors) and synthetic biological nanoparticles (BNP) (e.g., synthetically designed from different adeno-associated viruses, as well as other parvoviruses). The term "vector" includes both viral and nonviral plasmid) nucleic acid molecules for introducing a nucleic acid into a cell in vitro, ex vivo, and/or in vivo.

It will be apparent to those skilled in the art that any suitable vector can be used to deliver a heterologous nucleic acid of this invention. The choice of delivery vector can be made based on a number of factors known in the art, including age and species of the target host, in vitro vs. in vivo delivery, level and persistence of expression desired, intended purpose (e.g., for therapy or polypeptide production), the target cell or organ, route of delivery, size of the isolated nucleic acid, safety concerns, and the like.

Suitable vectors also include virus vectors (e.g., retrovirus, alphavirus; vaccinia virus; adenovirus, adeno-associated virus, or herpes simplex virus), lipid vectors, poly-lysine vectors, synthetic polyamino polymer vectors that are used with nucleic acid molecules, such as plasmids, and the like.

Protocols for producing recombinant viral vectors and for using viral vectors for nucleic acid delivery can be found, e.g., in *Current Protocols in Molecular Biology*, Ausubel, F. M. et al. (eds.) Greene Publishing Associates. (1989) and other standard laboratory manuals (e.g., Vectors for Gene Therapy. In: *Current Protocols in Human Genetics*. John Wiley and Sons, Inc.: 1997).

A large number of vectors known in the art may be used to manipulate nucleic acids, incorporate response elements and promoters into genes, etc. For example, the insertion of the nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini. Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences transgenes), e.g., one, two, three, four, five or more heterologous nucleotide sequences (e.g., a vector comprising the nucleotide sequence of SEQ ID NO:1).

In addition to a nucleic acid of interest (e.g., a synthetic polynucleotide of the invention), a vector may also comprise one or more regulatory regions, and/or selectable markers useful in selecting, measuring, and monitoring nucleic acid transfer results (delivery to specific tissues, duration of expression, etc.).

A vector comprising a synthetic polynucleotide of the invention may be used to infect and thereby delivering said synthetic polynucleotide to the infected cells. The exact method of introducing the synthetic polynucleotide into mammalian cells is, of course, not limited to the use of any particular type of vector. Any vector system now known or later identified may be used with the synthetic polynucleotides of this invention. Techniques are widely available for such procedures including the use of, for example, adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naldini et al., *Science* 272:263-267, 1996), and pseudotyped retroviral vectors (Agrawal et al., *Exper. Hematol.* 24:738-747, 1996). Also included are chimeric viral particles, which are well known in the art and which can comprise viral proteins and/or nucleic acids from two or more different viruses in any combination to produce a functional viral vector. Chimeric viral particles of this invention can also comprise amino acid and/or nucleotide sequence of non-viral origin (e.g., to facilitate targeting of vectors to specific cells or tissues and/or to induce a specific immune response).

Vectors may be introduced into the desired cells by methods known in the art, e.g., transfection, electroporation, microinjection, transduction, cell fusion, DEAE dextran, calcium phosphate precipitation, lipofection (lysosome fusion), use of a gene gun, or a nucleic acid vector transporter (see, e.g., \Vu et al., *J. Biol. Chem.* 267:963 (1992); Wu et al., *J. Biol. Chem.* 263:14621 (1988); and Hartmut et al., Canadian Patent Application No. 2,012,311, filed Mar. 15, 1990). In various embodiments, other molecules can be used for facilitating delivery of a nucleic acid in vivo, such as a cationic oligopeptide (e.g., WO95/21931), peptides derived from nucleic acid binding proteins (e.g., WO96/25508), and/or a cationic polymer (e.g., WO95/21931). It is also possible to introduce a vector in vivo as naked nucleic acid (see U.S. Pat. Nos. 5,693,622, 5,589,466 and 5,580,859). Receptor-mediated nucleic acid delivery approaches can also be used (Curiel et al., *Hum. Gene Ther.* 3:147 (1992); Wu et al., *J. Biol. Chem.* 262:4429 (1987)).

Thus, administration or delivery of a synthetic polynucleotide of this invention can be achieved by any one of numerous, well-known approaches, for example, but not limited to, direct transfer of the nucleic acids, in a plasmid or viral vector, or via transfer in cells or in combination with carriers such as cationic liposomes. Such methods are well known in the art and readily adaptable for use in the methods described herein. Furthermore, these methods can be used to target certain diseases and tissues, organs and/or cell types and/or populations by using the targeting characteristics of the carrier, which would be well known to the skilled artisan. It would also be well understood that cell and tissue specific promoters can be employed in the nucleic acids of this invention to target specific tissues and cells and/or to treat specific diseases and disorders.

As used herein, the terms "protein" and "polypeptide" are used interchangeably and encompass both peptides and proteins, unless indicated otherwise.

A "fusion protein" is a polypeptide produced when two heterologous nucleotide sequences or fragments thereof coding for two (or more) different polypeptides not found fused together in nature are fused together in the correct translational reading frame. Illustrative fusion polypeptides include fusions of a polypeptide of the invention (or a fragment thereof) to all or a portion of glutathione-S-transferase, maltose-binding protein, or a reporter protein (e.g., Green Fluorescent Protein, β-glucuronidase, β-galactosidase, luciferase, etc.), hemagglutinin, c-myc, FLAG epitope, etc.

As used herein, a "functional" polypeptide or "functional fragment" is one that substantially retains at least one biological activity normally associated with that polypeptide (e.g., angiogenic activity, protein binding, ligand or receptor binding). In particular embodiments, the "functional" polypeptide or "functional fragment" substantially retains all of the activities possessed by the unmodified peptide. By "substantially retains" biological activity, it is meant that the polypeptide retains at least about 20%, 30%, 40%, 50%, 60%, 75%, 85%, 90%, 95%, 97%, 98%, 99%, or more, of the biological activity of the native polypeptide (and can even have a higher level of activity than the native polypeptide). A "non-functional" polypeptide is one that exhibits little or essentially no detectable biological activity normally associated with the polypeptide (e.g., at most, only an insignificant amount, e.g., less than about 10% or even less than about 5%). Biological activities such as glycosylation of α-DG can be measured using assays that are well known in the art and as described herein (See, e.g., Xu, L. et al. "Adeno-associated virus 9 mediated FKRP gene therapy restores functional glycosylation of α-dystroglycan and improves muscle functions." *Mol. Ther.* 10, 1832-1840 (2013)).

By the term "express" or "expression" of a polynucleotide coding sequence, it is meant that the sequence is transcribed, and optionally, translated. Typically, according to the present invention, expression of a coding sequence of the invention will result in production of the polypeptide of the invention. The entire expressed polypeptide or fragment can also function in intact cells without purification.

The term "adeno-associated virus" (AAV) in the context of the present invention includes without limitation AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, and ovine AAV and any other AAV now known or later discovered. See, e.g., BERNARD N. FIELDS et al., VIROLOGY, volume 2, chapter 69 (4th ed., Lippincott-Raven Publishers). A number of additional AAV serotypes and clades have been identified (see, e.g., Gao et al., (2004)*J. Virol.* 78:6381-6388 and Table 1), which are also encompassed by the term "AAV."

The genomic sequences of various AAV and autonomous parvoviruses, as well as the sequences of the inverted terminal repeats (ITRs). Rep proteins, and capsid subunits are known in the art. Such sequences may be found in the literature or in public databases such as the GenBank® database. See, e.g., GenBank® Accession Numbers NC 002077, NC 001401, NC 001729, NC 001863, NC 001829, NC 001862, NC 000883, NC 001701, NC 001510, AF063497, U89790, AF043303, AF028705, AF028704, J02275, J01901, J02275, X01457, AF288061, AH009962, AY028226, AY028223, NC 001358, NC 001540, AF513851, AF513852, AY530579, AY631965, AY631966; the disclosures of which are incorporated herein in their entirety. See also, e.g., Srivistava et al., (1983) *J. Virol.* 45:555; Chiorini et al., (1998) *J. Virol.* 71:6823; Chiorini et al., (1999) *J. Virol.* 73:1309; Bantel-Schaal et al., (1999) *J. Virol.* 73:939; Xiao et al., (1999) *J. Virol.* 73:3994; Murarnatsu et al., (1996) *Virology* 221:208; Shade et al, (1986) *J. Virol.* 58:921; Gao et al., (2002) *Proc. Nat. Acad. Sci. USA* 99:11854; international patent publications WO 00/28061, WO 99/61601, WO 98/11244; U.S. Pat. No. 6,156,303; the disclosures of which are incorporated herein in their entirety. See also Table 1. An early description of the AAV1, AAV2 and AAV3 terminal repeat sequences is provided by Xiao, X., (1996), "Characterization of Adeno-associated virus (AAV) DNA replication and integration," Ph.D. Dissertation, University of Pittsburgh, Pittsburgh, Pa. (incorporated herein it its entirety).

A "recombinant AAV vector genome" or "rAAV genome" is an AAV genome (i.e., vDNA) that comprises at least one inverted terminal repeat e.g., one, two or three inverted terminal repeats) and one or more heterologous nucleotide sequences. rAAV vectors generally retain the 145 base terminal repeat(s) (TR(s)) in cis to generate virus; however, modified AAV TRs and non-AAV TRs including partially or completely synthetic sequences can also serve this purpose. All other viral sequences are dispensable and may be supplied in trans (Muzvczka, (1992) *Curr. Topics Microbiol. Immunol.* 158:97). The rAAV vector optionally comprises two TRs (e.g., AAV TRs), which generally will be at the 5' and 3' ends of the heterologous nucleotide sequence(s), but need not be contiguous thereto. The TRs can be the same or different from each other. The vector genome can also contain a single ITR at its 3' or 5' end.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or the SV40 hairpin that serves as the origin of SV40 replication can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

"AAV terminal repeat" or "AAV TR" may be from any AAV, including but not limited to serotypes 1, 2, 3, 4, 5, 6, 7, 8, 9, 10 or 11 or any other AAV now known or later discovered (see, e.g., Table 1). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

The terms "rAAV particle" and "rAAV virion" are used interchangeably here. A "rAAV particle" or "rAAV virion" comprises a rAAV vector genome packaged within an AAV capsid.

The AAV capsid structure is described in more detail in BERNARD N. FIELDS et al., VIROLOGY, volume 2, chapters 69 & 70 (4th ed., Lippincott-Raven Publishers).

The term "pharmacokinetic properties" has its usual and customary meaning and refers to the absorption, distribution, metabolism and excretion of FKRP.

As used herein, a "transformed" cell is a cell that has been transformed, transduced and/or transfected with an optimized synthetic polynucleotide of this invention encoding a FKRP.

As used herein, the term "dystroglycanopathy" refers to a subset of muscular dystrophies involving a reduction in glycoslation of alpha-dystroglycan (α-DG). Such disorders include but are not limited to limb girdle muscular dystrophy 2I, congenital muscular dystrophy, Walker-Warburg syndrome, or muscle-eye-brain disease.

A "subject" of the invention includes any animal having or susceptible to a dystroglycanopathy for which prevention or treatment of said dystroglycanopathy is needed and/or desired, which can be treated, ameliorated or prevented by administration/delivery of a synthetic polynucleotide of the invention encoding FKRP to the subject. Such a subject is generally a mammalian subject (e.g., a laboratory animal such as a rat, mouse, guinea pig, rabbit, primates, etc.), a farm or commercial animal (e.g, a cow, horse, goat, donkey, sheep, etc.), or a domestic animal (e.g., cat, dog, ferret, etc.). In particular embodiments, the subject is a primate subject, a non-human primate subject (e.g., a chimpanzee, baboon, monkey, gorilla, etc.) or a human. Subjects of the invention can be a subject known or believed to be at risk of dystroglycanopathy for Which prevention or treatment is needed and/or desired. Alternatively, a subject according to the invention can also include a subject not previously known or suspected to be at risk of dystroglycanopathy for which prevention or treatment is needed or desired. As a further option, the subject can be a laboratory animal and/or an animal model of disease. Suitable subjects include both males and females and subjects of any age, including embryonic (e.g., in utero or in ova), infant, juvenile, adolescent, adult and geriatric subjects.

A "subject in need thereof" in the context of treatment or therapy is a subject known to have, or suspected of having or being at risk of having, a disease or disorder (e.g., dystroglycanopathy), and that is likely to benefit from the treatment or therapy, i.e., is in need thereof.

Synthetic Polynucleotides, Expression Cassettes and Vectors

One aspect of the present invention relates to a synthetic polynucleotide encoding a human fukutin-related protein (FKRP), wherein the synthetic polynucleotide comprises, consists essentially of, or consists of: the nucleotide sequence of SEQ NO:1; and/or a nucleotide sequence having at least 90% identity to SEQ ID NO:1. In some embodiments, the nucleotide sequence is at least about 90%, 91%, 92%, 93%, 94%, 95%, 96%, 97%, 98%, or 99% identical to the nucleotide sequence of SEQ ID NO: 1.

In one embodiment, the synthetic polynucleotide encoding a FKRP comprises, consists essentially of, or consists of a nucleotide sequence encoding FKRP, wherein the GC content is reduced by about 5% to about 10% compared to the GC content of SEQ IF) NO:2 (e.g., 5%, 5.5%, 6%, 6.5%, 7%, 7.5%, 8%, 8.5%, 9%, 9.5%, 10%, or any range or value therein). The present inventors have surprisingly discovered that, contrary to what is commonly understood in the art of nucleic acid expression and protein production, wherein increasing GC content is understood to increase expression (Kudla et al., *PLos Biology* DOI: 10.1371/journal.pbio.0040180 (2006)), reducing the GC content of the polynucleotide encoding FKRP increases expression of said polynucleotide as compared to the native polynucleotide encoding FKRP, and thereby increasing production of FKRP as compared to the native polynucleotide encoding FKRP.

In additional aspects, a synthetic polynucleotide encoding FKRP (e.g., polynucleotide encoding SEQ ID NO:1 and/or a polynucleotide having at least about 90% identity to SEQ ID NO:1, and/or a polynucleotide encoding FKRP, wherein the GC content is reduced by about 5% to about 10% compared to the GC content of SEQ ID NO:2) may be operably associated with control or regulatory sequences. For example, the synthetic polynucleotide may be operably associated with expression control elements, such as promoters, transcription/translation control signals, origins of replication, polyadenylation signals, internal ribosome entry sites (IRES), enhancers, and the like.

In some embodiments, the synthetic polynucleotide encoding FKRP can be comprised in a vector or expression cassette in which the synthetic polynucleotide encoding FKRP is operably linked to a promoter.

Those skilled in the art will appreciate that a variety of promoter/enhancer elements may be used depending on the level and tissue-specific expression desired. The promoter/enhancer may be constitutive or inducible, depending on the pattern of expression desired. The promoter/enhancer may be native/endogenous or foreign/heterologous and can be a natural or a synthetic sequence. By foreign/heterologous, it is intended that the transcriptional initiation region is not found in the wild-type host into which the transcriptional initiation region is introduced.

Promoter/enhancer elements can be native/endogenous to the target cell or subject to be treated and/or native to the heterologous nucleic acid sequence. The promoter/enhancer element is generally chosen so that it will function in the target cell(s) of interest. In representative embodiments, the promoter/enhancer element is a mammalian promoter/enhancer element. The promoter/enhance element may be constitutive or inducible.

Inducible expression control elements are generally used in those applications in which it is desirable to provide regulation over expression of the heterologous nucleic acid sequence(s). Inducible promoter/enhancer elements include, but are not limited to, hormone-inducible and metal-inducible elements Promoters/enhancer elements for gene delivery can be tissue-specific or tissue-preferred promoter/enhancer elements, and include muscle specific or preferred (including cardiac, skeletal and/or smooth muscle), neural tissue specific or preferred (including brain-specific), eye (including retina-specific and cornea-specific), bone marrow specific or preferred, pancreatic specific or preferred, spleen specific or preferred, and lung specific or preferred promoter/enhancer elements.

Thus, any promoter operable in the organism or subject in which expression of the synthetic polynucleotide encoding FKRP is desired can be used. Promoters useful with this invention include, but are not limited to, a creatine kinase (CK) promoter, a chicken β-actin promoter (CB), desmine promoter, a actin promoter, or any viral promoter. In representative embodiments, the promoter can be a CK7 promoter. In some embodiments, a promoter can be modified to include other regulatory elements, for example, enhancer sequences. In other embodiments, the promoters are not modified to include other regulatory elements such as enhancers.

In representative embodiments, an enhancer sequence useful with this invention can include a CMV enhancer, SV40 enhancer, a muscle creatine kinase enhancer, and/or a myosin light chain enhancer, troponin promoter, tropomycin enhancer, and/or any other synthetic enhancer with or without modification.

In some embodiments, an expression system or construct can include a 3' untranslated region downstream of the nucleotide sequence encoding the desired recombinant protein. This region can increase expression of the transgene. Among the 3' untranslated regions useful in this regard are sequences that provide a poly A signal.

Another aspect of the invention is a vector, e.g., an expression vector, comprising the synthetic polynucleotide of the invention. The vector may be any type of vector known in the art, including, without limitation, plasmid vectors and viral vectors. In some embodiments, the viral vector is a retroviral or lentiviral vector. In some embodiments, the viral vector is an AAV vector from any known AAV serotype including without limitation AAV type 1, AAV type 2, AAV type 3 (including types 3A and 3B), AAV type 4, AAV type 5. AAV type 6, AAV type 7, AAV type 8, AAV type 9, AAV type 10, AAV type 11, avian AAV, bovine AAV, canine AAV, equine AAV, and ovine AAV and any other AAV now known or later discovered. In some embodiments, the AAV vector is AAV8 or AAV9.

In some embodiments, the AAV vector may be modified. Thus, for example, an AAV capsid protein of a virus vector can comprise a modification in the amino acid sequence in the three-fold axis loop 4 (Opie et al., *J. Virol.* 77: 6995-7006 (2003)). Such modifications have been shown to confer one or more desirable properties to virus vectors comprising the modified AAV capsid protein including without limitation (i) reduced transduction of liver, (ii) enhanced movement across endothelial cells, (iii) systemic transduction; (iv) enhanced transduction of muscle tissue (e.g., skeletal muscle, cardiac muscle and/or diaphragm muscle), and/or (v) reduced transduction of brain tissues (e.g., neurons). Thus, in representative embodiments, such modifications can reduce delivery of the synthetic polynucleotides of the invention to the liver (See, Asokan et al. *Nat Biotechnol.* 28(1):79-82 (2010); U.S. Pat. No. 8,889,641).

In some embodiments, the vector may further comprise a nucleic acid element that reduces expression in the liver. In representative embodiments, the vector further comprises a mir122 binding element. The mir122 sequence and its use to reduce expression in the liver is well known in the art (See, e.g., Qiao et al, *Gene Therapy* 18, 403-410 (April 2011) doi:10.1038/gt.2010.157).

A further aspect of the invention relates to a cell comprising the synthetic polynucleotide of the invention and/or vector comprising the synthetic polynucleotide of the invention (e.g., an isolated cell, a transformed cell, a recombinant cell, etc.). Thus, various embodiments of the invention are directed to recombinant host cells containing a vector (e.g., expression cassette) comprising the synthetic polynucleotide of the invention. Such a cell can be isolated and/or present in an animal, e.g, a transgenic animal. Transformation of cells is described further below.

Another aspect of the invention relates to a transgenic animal comprising the polynucleotide, vector, and/or transformed cell of the invention. A transgenic animal may include, but is not limited to, a farm animal (e.g., pig, goat, sheep, cow, horse, rabbit and the like), rodents (such as mice, rats and guinea pigs), and domestic pets (for example, cats and dogs). In some embodiments, the transgenic animal is not a human.

A transgenic animal may be produced by introducing into a single cell embryo the synthetic polynucleotide of the invention encoding FKRP (e.g., the nucleotide sequence of SEQ NO:1; and/or a nucleotide sequence having at least 90% identity to SEQ ID NO:1 and/or a nucleotide sequence encoding FKRP, wherein the GC content is reduced by about 5% to about 10% compared to the GC content of SEQ ID NO:2) in a manner such that the synthetic polynucleotide is stably integrated into the DNA of germ line cells of the mature animal, and is inherited in normal Mendelian fashion. The transgenic animal of this invention would have a phenotype of producing FKRP in body fluids and/or tissues. In some embodiments, the FKRP may be removed from these fluids and/or tissues and processed, for example for therapeutic use. (See. e.g., Clark et al. "Expression of human anti-hemophilic factor IX in the milk of transgenic sheep" *Bio/Technology* 7:487-492 (1989); Van Cott et al. "Haemophilic factors produced by transgenic livestock: abundance can enable alternative therapies worldwide" *Haemophilia* 10(4):70-77 (2004), the entire contents of which are incorporated by reference herein).

DNA molecules can be introduced into embryos by a variety of means including but not limited to microinjection, calcium phosphate mediated precipitation, liposome fusion, or retroviral infection of totipotent or pluripotent stem cells. The transformed cells can then be introduced into embryos and incorporated therein to form transgenic animals. Methods of making transgenic animals are described, for example, in *Transgenic Animal Generation and Use* by L. M. Houdebine, Harwood Academic Press, 1997. Transgenic animals also can be generated using methods of nuclear transfer or cloning using embryonic or adult cell lines as described for example in Campbell et al., *Nature* 380:64-66 (1996) and Wilmut et al., *Nature* 385:810-813 (1997). Further a technique utilizing cytoplasmic injection of DNA can be used as described in U.S. Pat. No. 5,523,222.

FKRP-producing transgenic animals can be obtained by introducing a chimeric construct comprising the synthetic polynucleotide of the invention (e.g., the nucleotide sequence of SEQ ID NO:1; and/or a nucleotide sequence having at least 90% identity to SEQ ID NO:1 and/or a nucleotide sequence encoding FKRP, wherein the GC content is reduced by about 5% to about 10% compared to the GC content of SEQ ID NO:2). Methods for obtaining transgenic animals are well-known. See, for example, Hogan et al., *Manipulating the Mouse Embryo*, (Cold Spring Harbor Press 1986); Krimpenfort et al., *Bio/Technology* 9:88 (1991); Palmiter et al., Cell 41:343 (1985), Kraemer et al., *Genetic Manipulation of the Early Mammalian Embryo*, (Cold Spring Harbor Laboratory Press 1985); Hammer et al., *Nature* 315:680 (1985); Wagner et al., U.S. Pat. No. 5,175,385; Krimpenfort et al., U.S. Pat. No. 5,175,384, Janne et al., *Ann, Med.* 24:273 (1992), Brem et al., *Chim. Oggi.* 11:21 (1993), Clark et al., U.S. Pat. No. 5,476,995, all incorporated by reference herein in their entireties.

The synthetic polynucleotide encoding FKRP, or vector and/or cell comprising said synthetic polynucleotide can be included in a pharmaceutical composition. Some embodiments are directed to a kit which includes said synthetic polynucleotide, or vector and/or cell comprising said synthetic polynucleotide of the invention and/or reagents and/or instructions for using the kit, e.g., to carry out the methods of this invention.

A further aspect of the invention relates to the use of the synthetic polynucleotides encoding FKRP, or vector, expression cassette, and/or cell comprising one or more synthetic polynucleotides encoding FKRP. Thus, one aspect relates to a method of producing a FKRP polypeptide in a cell or in a subject, comprising delivering to the cell or the subject the synthetic polynucleotide, vector, and/or transformed cell of the invention, thereby producing the FKRP polypeptide in said cell or said subject. The synthetic polynucleotide, vector, and/or transformed cell are delivered under conditions whereby expression of the synthetic polynucleotide encoding FKRP occurs to produce a FKRP polypeptide. Such conditions are well known in the art.

Methods

Another aspect provides a method of increasing glycosylation of alpha-dystroglycan ($\alpha$-DG) in a subject comprising, consisting essentially of, or consisting of: delivering to said subject a synthetic polynucleotide encoding (a) the nucleotide sequence of SEQ NO:1, and/or (b) a nucleotide sequence having at least 90% identity to SEQ ID NO:1, and/or (c) a nucleotide sequence encoding a human FKRP, wherein the GC content is reduced by about 5% to about 10% compared to the GC content of SEQ ID NO:2; and/or a vector comprising, consisting essentially of, or consisting of the synthetic polynucleotide, wherein the synthetic polynucleotide is expressed in the subject, thereby producing FKRP and increasing glycosylation of $\alpha$-DG.

A further aspect of the invention provides a method of delivering a nucleic acid to a cell comprising, consisting essentially of, or consisting of: delivering to the cell a synthetic polynucleotide encoding (a) the nucleotide sequence of SEQ ID NO:1, and/or (b) a nucleotide sequence having at least 90% identity to SEQ ID NO: 1, and/or (c) a nucleotide sequence encoding a human FKRP, wherein the GC content is reduced by about 5% to about 10% compared to the GC content of SEQ ID NO:2; and/or a vector comprising, consisting essentially of, or consisting of the synthetic polynucleotide. In some embodiments, the synthetic polynucleotide of the invention, and/or vector may be delivered to the cell in a therapeutically effective amount.

Another aspect of the invention provides a method of delivering a nucleic acid to a subject comprising, consisting essentially of, or consisting of: delivering to the subject a synthetic polynucleotide encoding (a) the nucleotide sequence of SEQ ID NO:1; and/or (b) a nucleotide sequence having at least 90% identity to SEQ ID NO:1, and/or (c) a nucleotide sequence encoding a human FKRP, wherein the GC content is reduced by about 5% to about 10% compared to the GC content of SEQ ID NO:2; a vector comprising, consisting essentially of, or consisting of the synthetic polynucleotide; and/or a transformed cell comprising, consisting essentially of, or consisting of the synthetic polynucleotide and/or said vector comprising, consisting essentially of, or consisting of the synthetic polynucleotide. In some embodiments, the synthetic polynucleotide of the invention, and/or vector and/or transformed cell may be delivered to the subject in a therapeutically effective amount.

A further aspect of the invention provides a method of treating a dystroglycanopathy in a subject in need thereof, comprising delivering to the subject a therapeutically effective amount of a synthetic polynucleotide encoding (a) the nucleotide sequence of SEQ ID NO:1, and/or (b) a nucleotide sequence having at least 90% identity to SEQ ID NO:1, and/or (c) a nucleotide sequence encoding a human FKRP, wherein the GC content is reduced by about 5% to about 10% compared to the GC content of SEQ ID NO:2; and/or a vector comprising, consisting essentially of, or consisting of the synthetic polynucleotide, and/or a transformed cell comprising, consisting essentially of, or consisting of the synthetic polynucleotide and/or the vector, thereby treating dystroglycanopathy in the subject. In some embodiments, the dystroglycanopathy comprises, consists essentially of, or consists of a mutation in the native or endogenous nucleic acid encoding FKRP and/or a deficiency in glycosylation of alpha-dystroglycan (α-DG), or any combination thereof. In some embodiments, the dystroglycanopathy can include, but is not limited to, limb girdle muscular dystrophy 2I, congenital muscular dystrophy, Walker-Warburg syndrome, muscle-eye-brain disease, and/or any combination thereof.

In embodiments of the invention, the dosage of a vector (e.g., a viral vector or other nucleic acid vector) encoding a FKRP (e.g., comprising, consisting essentially of, or consisting of the nucleotide sequence of SEQ ID NO:1, and/or a nucleotide sequence having at least 90% identity to SEQ ID NO:1; and/or a nucleotide sequence encoding human FKRP, wherein the GC content is reduced by about 5% to about 10% compared to the GC content of SEQ ID NO:2) can be in an amount such that a therapeutic plasma concentration of FKRP is achieved. The dosage can be about $1\times10^{12}$ vector particles/per kg body weight to about $1\times10^{15}$ vector particles/per kg body weight (e.g., $10^{12}$, $10^{13}$, $10^{14}$, $10^{15}$ vector particles/per kg body weight, and any range or value therein). One of skill in the art would be able to determine the optimal dose for a given subject and a given condition.

In some embodiments, a synthetic polynucleotide encoding FKRP (e.g., the nucleotide sequence of SEQ ID NO:1, and/or a nucleotide sequence having at least 90% identity to SEQ ID NO:1, and/or a nucleotide sequence encoding human FKRP, wherein the GC content is reduced by about 5% to about 10% compared to the GC content of SEQ ID NO:2) can be delivered to the subject using an AAV vector. Thus, the invention also provides AAV virus particles (i.e., virions) comprising the synthetic polynucleotide encoding FKRP, wherein the virus panicle packages (i.e., encapsidates) a vector genome, optionally an AAV vector genome.

In particular embodiments, the virion may be a recombinant vector comprising the synthetic polynucleotide encoding human FKRP, e.g., for delivery to a cell. Thus, the present invention is useful for the delivery of polynucleotides to cells in vitro, ex vivo, and in vivo. In representative embodiments, the recombinant vector of the invention can be advantageously employed to deliver or transfer polynucleotides to animal (e.g., mammalian) cells.

A vector can further encode reporter polypeptides (e.g., an enzyme). Reporter polypeptides are known in the art and include, but are not limited to, a fluorescent protein (e.g., EGFP, GFP, RFP, BFP, YFP, or dsRED2), an enzyme that produces a detectable product, such as luciferase (e.g., from *Gaussia*, *Renilla*, or *Photinus*), β-galactosidase, β-glucuronidase, alkaline phosphatase, and chloramphenicol acetyltransferase gene, or proteins that can be directly detected. Virtually any protein can be directly detected by using, for example, specific antibodies to the protein. Additional markers (and associated antibiotics) that are suitable for either positive or negative selection of eukaryotic cells are disclosed in Sambrook and Russell (2001), *Molecular Cloning*, 3rd Ed., Cold Spring Harbor Laboratory Press, Cold Spring Harbor, N.Y., and Ausubel et al. (1992), *Current Protocols in Molecular Biology*, John Wiley & Sons, including periodic updates.

The present invention further provides methods of producing the virus vectors of the invention. In a representative embodiment, the present invention provides a method of producing a recombinant virus vector, the method comprising providing to a cell in vitro, (a) a template comprising (i) a synthetic polynucleotide encoding human FKRP (e.g., the nucleotide sequence of SEQ ID NO:1, a nucleotide sequence having at least 90% identity to SEQ ID NO:1, a nucleotide sequence encoding human FKRP, wherein the GC content is reduced by about 5% to about 10% compared to the GC content of SEQ ID NO:2), and (ii) packaging signal sequences sufficient for the encapsidation of the AAV template into virus particles (e.g, one or more (e.g., two) terminal repeats, such as AAV terminal repeats), and (b) AAV sequences sufficient for replication and encapsidation of the template into viral particles (e.g., the AAV rep and AAV cap sequences). The template and AAV replication and capsid sequences are provided under conditions such that recombinant virus particles comprising the template packaged within the capsid are produced in the cell. The method can further comprise the step of collecting the virus particles from the cell. Virus particles may be collected from the medium and/or by lysing the cells.

In one illustrative embodiment, the invention provides a method of producing a rAAV particle comprising an AAV capsid, the method comprising: providing a cell in vitro with a nucleic acid encoding an AAV capsid, an AAV rep coding sequence, an AAV vector genome comprising a synthetic polynucleotide encoding human FKRP (e.g, the nucleotide sequence of SEQ ID NO:1, a nucleotide sequence having at least 90% identity to SEQ ID NO:1, a nucleotide sequence encoding FKRP, wherein the GC content is reduced by about 5% to about 10% compared to the GC content of SEQ ID NO:2), and helper functions for generating a productive AAV infection; and allowing assembly of the AAV particles comprising the AAV capsid and encapsidating the AAV vector genome.

The cell is typically a cell that is permissive for AAV viral replication. Any suitable cell known in the art may be employed, such as mammalian cells. Also suitable are trans-complementing packaging cell lines that provide functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an EBV based nuclear episome.

As a further alternative, the rep/cap sequences may be stably carried (episomal or integrated) within a cell.

Typically, the AAV rep/cap sequences will not be flanked by the AAV packaging sequences (e.g., AAV ITRs), to prevent rescue and/or packaging of these sequences.

The template (e.g., an rAAV vector genome) can be provided to the cell using any method known in the art. For example, the template may be supplied by a non-viral (e.g., plasmid) or viral vector. In particular embodiments, the template is supplied by a herpesvirus or adenovirus vector e.g., inserted into the E1a or E3 regions of a deleted adenovirus). As another illustration, Palombo et al., (1998) *J. Virol.* 72:5025, describe a baculovirus vector carrying a reporter gene flanked by the AAV ITRs. EBV vectors may also be employed to deliver the template, as described above with respect to the rep/cap genes.

In another representative embodiment, the template is provided by a replicating rAAV virus. In still other embodiments, an AAV provirus is stably integrated into the chromosome of the cell.

To obtain maximal virus titers, helper virus functions (e.g., adenovirus or herpesvirus) essential for a productive AAV infection are generally provided to the cell. Helper virus sequences necessary for AAV replication are known in the art. Typically, these sequences are provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes required for efficient AAV production as described by Ferrari et al., (1997) *Nature Med.* 3:1295, and U.S. Pat. Nos. 6,040,183 and 6,093,570.

Further, the helper virus functions may be provided by a packaging cell with the helper genes integrated in the chromosome or maintained as a stable extrachromosomal element. In representative embodiments, the helper virus sequences cannot be packaged into AAV virions, e.g., are not flanked by AAV ITRs.

Those skilled in the art will appreciate that it may be advantageous to provide the AAV replication and capsid sequences and the helper virus sequences (e.g., adenovirus sequences) on a single helper construct. This helper construct may be a non-viral or viral construct, but is optionally a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector further contains the rAAV template. The AAV rep/cap sequences and/or the rAAV template may be inserted into a deleted region (e.g., the E1a or E3 regions) of the adenovirus.

In a further embodiment, the AAV rep/cap sequences and the adenovirus helper sequences are supplied by a single adenovirus helper vector. The rAAV template is provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as a "EBV based nuclear episome," see Margolski, (1992) *Curr. Top. Microbiol. Immun.* 158:67).

In a further exemplary embodiment, the AAV rep/cap sequences and adenovirus helper sequences are provided by a single adenovirus helper. The rAAV template is provided as a separate replicating viral vector. For example, the rAAV template may be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids. As described above, in representative embodiments, the adenovirus helper sequences and the AAV rep/cap sequences are not flanked by the AAV packaging sequences (e.g., the AAV ITRs), so that these sequences are not packaged into the AAV virions.

Herpesvirus may also be used as a helper virus in AAV packaging methods. Hybrid herpesviruses encoding the AAV rep protein(s) may advantageously facilitate for more scalable AAV vector production schemes. A hybrid herpes simplex virus type I (HSV-1) vector expressing the AAV-2 rep and cap genes has been described (Conway et al., (1999) *Gene Therapy* 6:986 and WO 00/17377, the disclosures of which are incorporated herein in their entireties).

As a further alternative, the virus vectors of the invention can be produced in insect cells using baculovirus vectors to deliver the rep/cap genes and rAAV template as described by Urabe et al., (2002) *Human Gene Therapy* 13:1935-43.

Other methods of producing AAV use stably transformed packaging cells (see, e.g., U.S. Pat. No. 5,658,785).

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al., (1999) *Gene Therapy* 6:973). In representative embodiments, deleted replication-detective helper viruses are used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

The inventive packaging methods may be employed to produce high titer stocks of virus particles. In particular embodiments, the virus stock has a titer of at least about $10^5$ transducing units (tu)/ml, at least about $10^6$ tu/ml, at least about $10^7$ tu/ml, at least about $10^8$ tu/ml, at least about $10^9$ tu/ml, at least about $10^{10}$ tu/ml, at least about $10^{11}$ tu/ml, at least about $10^{12}$ tu/ml and at least about $10^{13}$ tu/ml, or at least about $10^{14}$ tu/ml.

In particular embodiments, the present invention provides a pharmaceutical composition comprising a virus vector of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form.

By "pharmaceutically acceptable" it is meant a material that is not toxic or otherwise undesirable, i.e., the material may be administered to a subject without causing any undesirable biological effects. A "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include, without limitation, any of the standard pharmaceutical carriers such as phosphate buffered saline solutions, water, emulsions such as oil/water emulsion, microemulsions and various types of wetting agents. In certain embodiments, the pharmaceutically acceptable carrier is sterile and would be deemed suitable for administration into human subjects according to regulatory guidelines for pharmaceutical compositions comprising the carrier.

One aspect of the present invention is a method of transferring a synthetic polynucleotide of the invention to a cell in vitro. The virus vector may be introduced to the cells at the appropriate multiplicity of infection according to standard transduction methods appropriate for the particular target cells. Titers of the virus vector to administer can vary, depending upon the target cell type and number, and the particular virus vector can be determined by those of skill in the art without undue experimentation. In particular embodiments, at least about 1 infectious unit, more preferably at least about 2 or more infectious units are introduced to one target cell.

The cell(s) into which the virus vector can be introduced may be of any type, including but not limited to neural cells (including cells of the peripheral and central nervous systems, in particular, brain cells such as neurons, oligodendrocytes, glial cells, astrocytes), lung cells, cells of the eye (including retinal cells, retinal pigment epithelium, and corneal cells), epithelial cells (e.g., gut and respiratory epithelial cells), skeletal muscle cells (including myoblasts, myotubes and myofibers), diaphragm muscle cells, dendritic cells, pancreatic cells (including islet cells), hepatic cells, a cell of the gastrointestinal tract (including smooth muscle cells, epithelial cells), heart cells (including cardiomyocytes), bone cells (e.g., bone marrow stem cells), hematopoietic stem cells, spleen cells, keratinocytes, fibroblasts, endothelial cells, prostate cells, joint cells (including, e.g., cartilage, meniscus, synovium and bone marrow), germ cells, and the like. Alternatively, the cell may be any progenitor cell. As a further alternative, the cell can be a stem cell (e.g., neural stem cell). As still a further alternative, the cell may be a cancer or tumor cell (cancers and tumors are described above). Moreover, the cells can be from any species of origin, as indicated above.

The virus vectors may be introduced to cells in vitro for the purpose of administering/delivering the modified cell to a subject. In particular embodiments, the cells have been removed from a subject, the virus vector is introduced therein, and the cells are then replaced back into the subject. Methods of removing cells from subject for treatment ex vivo, followed by introduction back into the subject are known in the art (see, e.g., U.S. Pat. No. 5,399,346). Alternatively, the recombinant virus vector is introduced into cells from another subject, into cultured cells, or into cells from any other suitable source, and the cells are administered to a subject in need thereof.

Suitable cells for ex vim gene therapy are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ or about $10^3$ to about $10^6$ cells will be administered per dose in a pharmaceutically acceptable carrier. In particular embodiments, the cells transduced with the virus vector are administered to the subject in an effective amount in combination with a pharmaceutical carrier.

A further aspect of the invention is a method of administering the virus vectors of the invention to a subject. In particular embodiments, the method comprises, consists essentially of, or consists of: administering an effective amount of a virus vector according to the invention to an animal subject. Administration of the virus vectors of the present invention to a human subject or an animal in need thereof can be by any means known in the art. Optionally, the virus vector is delivered in an effective dose in a pharmaceutically acceptable carrier.

An effective amount of a composition of this invention will vary from composition to composition and subject to subject, and will depend upon a variety of factors such as age, species, gender, weight, overall condition of the subject, and the particular disease or disorder to be treated. An effective amount can be determined in accordance with routine pharmacological procedures know to those of ordinary skill in the art. In some embodiments, a dose ranging from about $1 \times 10^{12}$ vector particles/per kg body weight to about $1 \times 10^{15}$ vector particles/per kg body weight will have therapeutic efficacy. In embodiments employing viral vectors for delivery of the nucleic acid of this invention, viral doses can be measured to include a particular number of virus particles or plaque forming units (pfu) or infectious particles, depending on the virus employed. For example, in some embodiments, particular unit doses can include about $10^3$ to about $10^{16}$ pfu or infectious particles per kg body weight (e.g., about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$ or $10^{16}$ pfu or infectious particles per kg body weight), or any range or value therein. Further exemplary doses for achieving therapeutic effects are virus titers can be at least about $10^5$ to about $10^{15}$ transducing units per kg body weight (e.g., at least about $10^5$, $10^6$, $10^7$, $10^8$, $10^9$, $10^{10}$, $10^{11}$, $10^{12}$, $10^{13}$, $10^{14}$, $10^{15}$ transducing units per kg body weight) or any range or value therein. In representative embodiments, doses for achieving therapeutic effects are virus titers can be at least about $10^8$ to about $10^{15}$ transducing units per kg body weight (e.g., about $10^8$, $10^9$, $10^{10}$, $10^{11}$, $10^{12}$, $10^{13}$, or $10^{14}$, $10^{15}$ transducing units per kg body weight) or any range or value therein. As the skilled artisan would understand, the specific dose would depend on the size of the target/subject and the nature of the target/subject.

The frequency of administration of a composition of this invention can be as frequent as necessary to impart the desired therapeutic effect. For example, the composition can be administered one, two, or more times per day, one, two, three, four or more times a week, one, two, three, four or more times a month, one, two, three or four times a year and/or as necessary to control a particular condition and/or to achieve a particular effect and/or benefit. In particular embodiments, more than one administration (e.g., two, three, four or more administrations) may be employed to achieve the desired level of gene expression over a period of various intervals, e.g., daily, weekly, monthly, yearly, etc. In some embodiments, one, two, three or four doses over the lifetime of a subject can be adequate to achieve the desired therapeutic effect. The amount and frequency of administration of the composition of this invention will vary depending on the particular condition being treated or to be prevented and the desired therapeutic effect.

Exemplary modes of administration include oral, rectal, transmucosal, topical, intranasal, inhalation (e.g., via an aerosol), buccal (e.g., sublingual), vaginal, intrathecal, intraocular, in utero (or in ovo), parenteral (e.g., intravenous, subcutaneous, intradermal, intramuscular [including administration to skeletal, diaphragm and/or cardiac muscle], intrapleural, intracerebral, and intraarticular), topical (e.g., to both skin and mucosal surfaces, including airway surfaces, and transdermal administration), and the like, as well as direct tissue or organ injection (e.g., to skeletal muscle, cardiac muscle, diaphragm muscle or brain). The most suitable route in any given case will depend on the nature and severity of the condition being treated and on the nature of the particular vector that is being used. In representative embodiments, the route of delivery for treatment of dystroglycanopay is intramuscular, intravenous and intraarterial to a part of or the whole body.

Delivery to any of these tissues can also be achieved by delivering a depot comprising the virus vector, which can be implanted into the tissue or the tissue can be contacted with a film or other matrix comprising the virus vector. Examples of such implantable matrices or substrates are described in U.S. Pat. No. 7,201,898.

Injectables can be prepared in conventional forms, either as liquid solutions or suspensions, solid forms suitable for solution or suspension in liquid prior to injection, or as emulsions. Alternatively, one may administer the virus vector in a local rather than systemic manner, for example, in a depot or sustained-release formulation. Further, the virus vector can be delivered dried to a surgically implantable matrix such as a bone graft substitute, a suture, a stent, and the like (e.g., as described in U.S. Pat. No. 7,201,898).

Pharmaceutical compositions suitable for oral administration can be presented in discrete units, such as capsules, cachets, lozenges, or tablets, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a virus vector of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sublingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions suitable for parenteral administration can comprise sterile aqueous and non-aqueous injection solutions of the composition of this invention, which preparations are optionally isotonic with the blood of the intended recipient. These preparations can contain antioxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit/dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 µg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration can be presented as unit dose suppositories. These can be prepared by admixing the composition with one or more conventional solid carriers, such as for example, cocoa butter and then shaping the resulting mixture.

Pharmaceutical compositions of this invention suitable for topical application to the skin can take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, *Pharm. Res.* 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

The virus vectors disclosed herein may be administered to the lungs of a subject by any suitable means, for example, by administering an aerosol suspension of respirable particles comprised of the virus vectors, which the subject inhales. The respirable particles may be liquid or solid. Aerosols of liquid particles comprising the virus vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors may likewise be produced with any solid particulate medicament aerosol generator, by techniques known in the pharmaceutical art.

Having described the present invention, the same will be explained in greater detail in the following examples, which are included herein for illustration purposes only, and which are not intended to be limiting to the invention.

EXAMPLES

Example 1. Synthetic Polynucleotide Encoding FKRP

We have designed and fully synthesized synthetic codon optimized polynucleotides encoding FKRP. The synthetic polynucleotides of the invention can be initially chemically synthesized with methods that are well known in the art and then can be incorporated into any vector for propagation. The synthetic polynucleotides together with any or all other vector elements can also be entirely chemically synthesized.

An alignment showing the differences between an optimized synthetic polynucleotide encoding FKRP of the invention (SEQ ID NO:1) and native polynucleotide encoding FKRP (SEQ ID NO:2) is provided below in Table 2.

Example 2. Vectors Comprising the Optimized Synthetic Polynucleotides

The synthetic polynucleotides can be biochemically incorporated into any vector containing any or all of elements necessary for the expression of the polypeptide encoded by the synthetic polynucleotides. The vector can then be propagated through well known biological systems to obtain any amount required for any purpose. The synthetic polynucleotides can also be chemically synthesized together with any or all of elements of a vector which can then be applied directly for the expression of the polypeptide encoded by the synthetic polynucleotides.

Example 3. Transformation of Cells

The synthetic polynucleotides in an expression vector can be used to transfect by polymer-mediated, or electroporation mediated methods, or infect muscle derived cells, or stem cells. The cells can then be established, selected, propagated for any therapeutic purpose, or for further model development.

Figure 2:
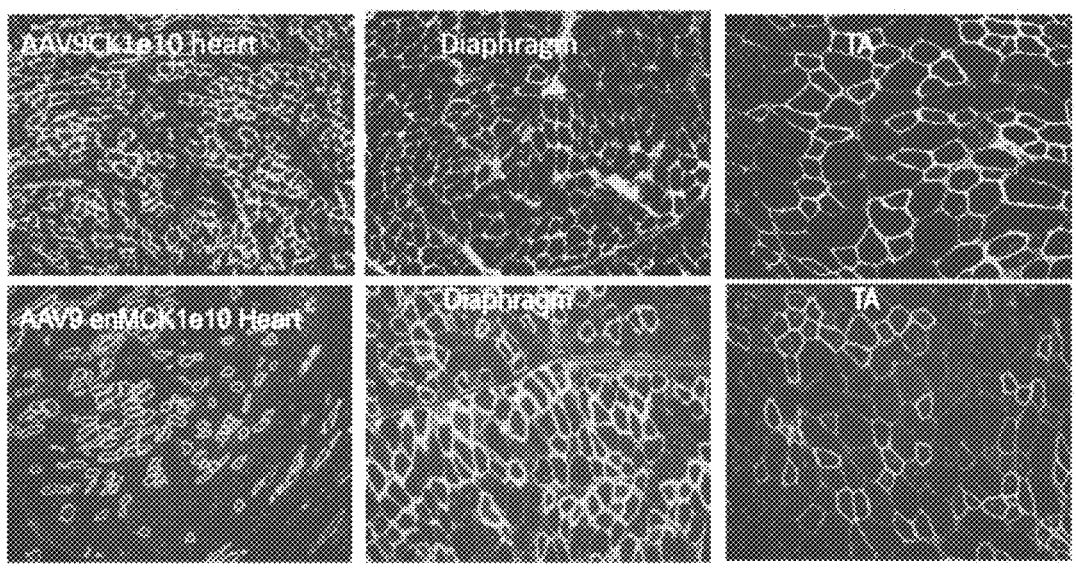
FIG. 2 shows the results of an in vivo test in FKRP mutant mouse models. FKRP mutant mice with P448L mutation were treated with the AAV9-CK7 promoter-codon optimized Human FKRP-mir122 target sites (AAV9 CK7, upper panel) and NICK enhancer-Syn100 promoter-codon-optimized human FKRP gene-mir122 target sites (AAV9enMCK, lower panel). The mice were treated with 1e10v.g./g systemically and three muscles were examined 1 month after the treatment.
Figure 3A:
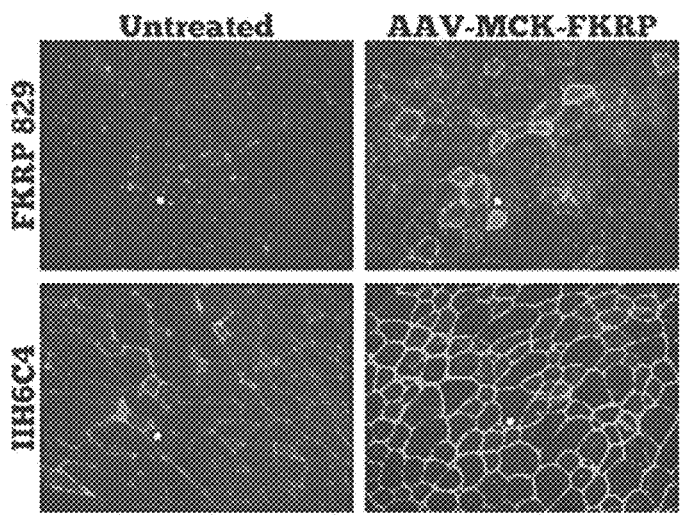
FIGS. 3A-3B shows FKRP mutant mice without clear expression of functional glycosylation in muscle tissue of both skeletal muscle (FIG. 3A, upper and lower left panels) and heart (FIG. 3B, upper and lower left panels). One month after AAV9 treatment with a MCK enhancer-Syn100 promoter-codon-optimized synthetic polynucleotide encoding human FKRP gene-mir122 target sites (AAV-MCK-FKRP) shows expression of FKRP (FIG. 3A-3B, upper and lower right panels). The AAV9 vector includes the mir122 targeting sequence for reducing FKRP expression in the liver. FKRPS29 is the antibody used to detect the AAV9 vector expressed human FKRP; IIH6 is the antibody detecting the glycosylated alpha dystroglycan on muscle fiber membrane.
Figure 3B:
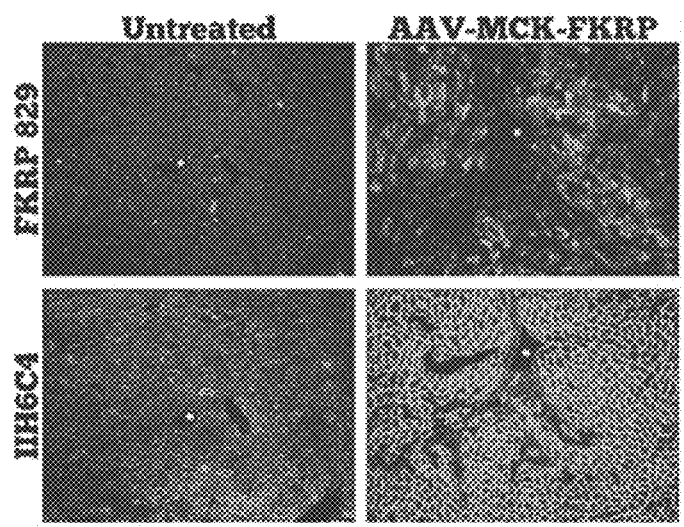

FIG. 1 shows FKRP mutations and reduced glycosylation of α-DG in limb girdle muscular dystrophy 2I (LGMD2I) as compared to normal tissue using immunofluorescence staining. FIG. 2 shows the results of an in vivo test in FKRP mutant mouse models. FKRP mutant mice with P448l mutation were treated with the AAV9-CK7 promoter-codon optimized human FKRP-mir122 target sites (AAV9 CK7) and MCK enhancer-Syn100 promoter-codon-optimized human FKRP gene-mir122 target sites (AAV9enMCK). The mice were treated with 1e10v.g./g systemically and three muscles were examined 1 month after the treatment. FIGS. 3A-3B shows FKRP mutant mice without clear expression of functional glycosylation in muscle tissue of both skeletal muscle. One month after AAV9 treatment with a MCK enhancer-Syn100 promoter-codon-optimized synthetic polynucleotide encoding human FKRP gene-mir122 target sites (AAV-MCK-FKRP), expression of FKRP is observed (FIGS. 3A-3B, upper and lower right panels).

Example 4. Treadmill Tests of Treated Mice

FKRPP448L mutant mice were treated with AAV9-human codon optimized FKRP-mir122 and Treadmill tests were carried out.

Figure 4:
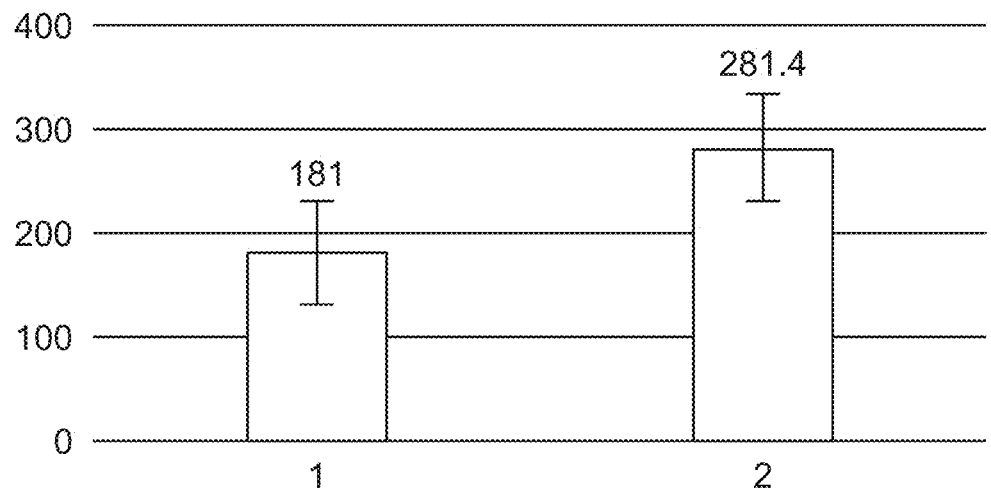
FIG. 4 shows functional improvement of the FKRPP448L mutant mice 6 months after the AAV9-human codon optimized FKRP-mir122 treatment in treadmill tests. The upper panel shows running distance and the lower panel show running time. "1" provides the results for the untreated age matched control mice and "2" provides the results for the AAV9-hFKRP treated mice.
Figure 4:
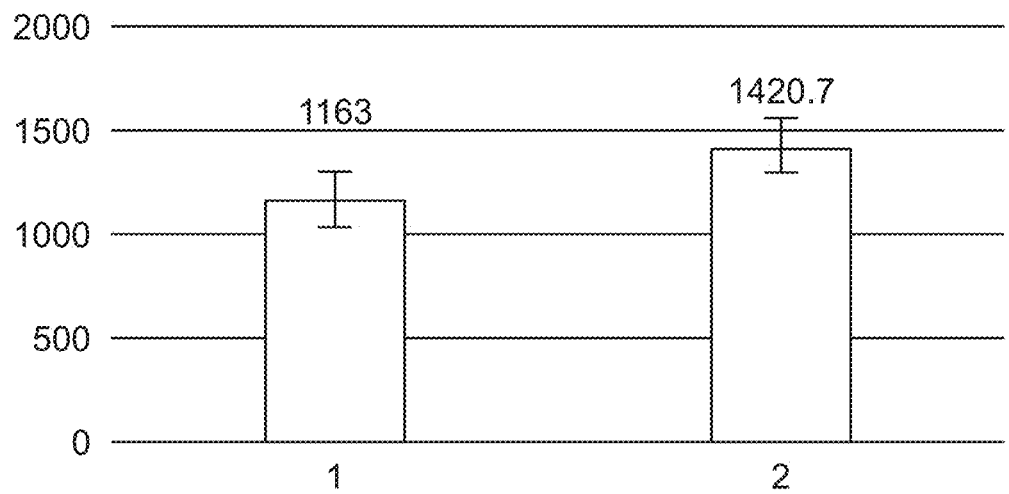

FIG. 4 shows functional improvement of the FKRPP448L mutant mice 6 months after the AAV9-human codon optimized FKRP-mir122 treatment ($5 \times 10^3$ $^{v.p.}$/kg). The mice were treated with the AAV9-human codon optimized FKRP-mir122 systemically by intravenous (i.v.) injection. The "1" in both the upper and lower panels of FIG. 4 refers to the untreated age matched control mice and the "2" refers to the AAV9-hFKRP treated mice. The treadmill tests demonstrate significant improvement in running time and distance for the treated in comparison with the controls.

It will be understood by those of skill in the art that numerous and various modifications can be made without departing from the spirit of the present invention. Therefore, it should be clearly understood that the forms of the present invention are illustrative only and are not intended to limit the scope of the present invention.

All publications, patent applications, patents, patent publications, sequences identified by GenBank® database accession numbers and other references cited herein are incorporated by reference in their entireties for the teachings relevant to the sentence and/or paragraph in which the reference is presented.

The foregoing is illustrative of the present invention, and is not to be construed as limiting thereof. The invention is defined by the following claims, with equivalents of the claims to be included therein.

Optimized nucleotide sequence encoding human FKRP 1488 nucleotides):

(SEQ ID NO: 1)

ATG AGA CTG ACA AGA TGC CAG GCC GCC CTG GCC GCT
GCC ATC ACA CTG AAT CTG CTG GTG CTG TTC TAT GTG
TCC TGG CTG CAG CAC CAG CCC CGG AAC TCT AGA GCC
AGA GGC CCA AGA AGG GCC TCT GCC GCC GGA CCT AGA
GTG ACA GTG CTC GTG CGC GAG TTC GAG GCC TTC GAC
AAT GCC GTG CCC GAG CTG GTG GAC AGC TTC CTG CAG
CAA GAC CCT GCT CAG CCT GTG GTG GTG GCC GCC GAT
ACA CTG CCT TAT CCT CCA CTG GCC CTG CCC AGA ATC
CCC AAT GTG CGA CTG GCT CTG CTG CAG CCC GCC CTG
GAT AGA CCT GCC GCC GCT AGC AGA CCT GAG ACA TAC
GTG GCC ACC GAG TTC GTG GCC CTG GTG CCT GAT GGC
GCC AGA GCT GAA GCT CCC GGC CTG CTG GAA AGA ATG
GTG GAA GCC CTG AGA GCC GGC AGC GCC AGA CTG GTG
GCT GCT CCT GTG GCT ACC GCC AAC CCT GCC AGA TGT
CTG GCC CTG AAT GTG TCC CTG AGA GAG TGG ACC GCC
AGA TAC GGC GCT GCC CCT GCC GCT CCT AGA TGT GAT
GCT CTG GAT GGC GAC GCC GTG GTG CTG CTG AGA GCC
AGG GAC CTG TTC AAC CTG AGC GCC CCT CTG GCC AGA
CCT GTG GGC ACA AGC CTG TTT CTG CAG ACA GCC CTG
AGG GGC TGG GCC GTG CAG CTG CTG GAT CTG ACA TTT
GCC GCT GCC AGA CAG CCT CCT CTG GCC ACA GCC CAT
GCC AGA TGG AAG GCC GAG AGA GAG GGC AGA GCC AGA
AGG GCT GCT CTG CTG AGG GCC CTG GGC ATC AGA CTG
GTG TCT TGG GAA GGC GGC AGA CTC GAG TGG TTC GGC
TGC AAC AAA GAA ACC ACC CGG TGC TTC GGC ACC GTC
GTG GGC GAT ACA CCA GCC TAC CTG TAC GAG GAA AGA
TGG ACC CCC CCT TGC TGC CTG CGG GCC CTG AGA GAA
ACA GCC AGA TAT GTC GTG GGC GTG CTG GAA GCC GCT
GGC GTG CGA TAT TGG CTG GAA GGC GGA TCT CTG CTG
GGA GCC GCC AGG CAC GGC GAC ATC ATC CCT TGG GAC
TAC GAC GTG GAC CTG GGC ATC TAC CTG GAA GAT GTG
GGC AAC TGC GAG CAG CTG AGA GGC GCC GAA GCC GGC
TCT GTG GTG GAT GAG AGG GGC TTC GTG TGG GAG AAG
GCC GTG GAA GGC GAC TTC TTC CGG GTG CAG TAC AGC
GAG AGC AAC CAT CTG CAT GTG GAC CTG TGG CCC TTC
TAC CCC CGG AAC GGC GTG ATG ACC AAG GAC ACC TGG
CTG GAC CAC CGG CAG GAC GTG GAA TTC CCC GAG CAC
TTT CTG CAG CCC CTG GTG CCA CTG CCT TTC GCC GGA
TTT GTG GCC CAG GCC CCC AAC AAC TAC CGG CGG TTC
CTG GAA CTG AAG TTC GGC CCT GGC GTG ATC GAG AAC
CCC CAG TAC CCT AAC CCT GCC CTG CTG AGC CTG ACC
GGC AGC GGC TAA

Native nucleotide sequence encoding human FKRP: (1488 nucleotides)

(SEQ ID NO: 2)

ATG CGG CTC ACC CGC TGC CAG GCT GCC CTG GCG GCC
GCC ATC ACC CTC AAC CTT CTG GTC CTC TTC TAT GTC
TCG TGG CTG CAG CAC CAG CCT AGG AAT TCC CGG GCC
CGG GGG CCC CGT CGT GCC TCT GCT GCC GGC CCC CGT
GTC ACC GTC CTG GTG CGG GAG TTC GAG GCA TTT GAC
AAC GCG GTG CCC GAG CTG GTA GAC TCC TTC CTG CAG
CAA GAC CCA GCC CAG CCC GTG GTG GTG GCA GCC GAC
ACG CTC CCC TAC CCG CCC CTG GCC CTG CCC CGC ATC
CCC AAC GTG CGT CTG GCG CTG CTC CAG CCC GCC CTG
GAC CGG CCA GCC GCA GCC TCG CGC CCG GAG ACC TAC
GTG GCC ACC GAG TTT GTG GCC CTA GTA CCT GAT GGG
GCG CGG GCT GAG GCA CCT GGC CTG CTG GAG CGC ATG
GTG GAG GCG CTC CGC GCA GGA AGC GCA CGT CTG GTG
GCC GCC CCG GTT GCC ACG GCC AAC CCT GCC AGG TGC
CTG GCC CTG AAC GTC AGC CTG CGA GAG TGG ACC GCC
CGC TAT GGC GCA GCC CCC GCC GCG CCC CGC TGC GAC
GCC CTG GAC GGA GAT GCT GTG GTG CTC CTG CGC GCC
CGC GAC CTC TTC AAC CTC TCG GCG CCC CTG GCC CGG
CCG GTG GGC ACC AGC CTC TTT CTG CAG ACC GCC CTT
CGC GGC TGG GCG GTG CAG CTG CTG GAC TTG ACC TTC
GCC GCG GCG CGC CAG CCC CCG CTG GCC ACG GCC CAC
GCG CGC TGG AAG GCT GAG CGC GAG GGA CGC GCT CGG
CGG GCG GCG CTG CTC CGC GCG CTG GGC ATC CGC CTA
GTG AGC TGG GAA GGC GGG CGG CTG GAG TGG TTC GGC
TGC AAC AAG GAG ACC ACG CGC TGC TTC GGA ACC GTG
GTG GGC GAC ACG CCC GCC TAC CTC TAC GAG GAG CGC
TGG ACG CCC CCT GCT GCC TGC GCG CTG CGC GAG
ACC GCC CGC TAT GTG GTG GGC GTG CTG GAG GCT GCG
GGC GTG CGC TAC TGG CTC GAG GGC GGC TCA CTG CTG
GGG GCC GCC CGC CAC GGG GAC ATC ATC CCA TGG GAC
TAC GAC GTG GAC CTG GGC ATC TAC TTG GAG GAC GTG
GGC AAC TGC GAG CAG CTG CGG GGG GCA GAG GCC GGC
TCG GTG GTG GAT GAG CGC GGC TTC GTA TGG GAG AAG
GCG GTC GAG GGC GAC TTT TTC CGC GTG CAG TAC AGC
GAA AGC AAC CAC TTG CAC GTG GAC CTG TGG CCC TTC
TAC CCC CGC AAT GGC GTC ATG ACC AAG GAC ACG TGG

```
CTG GAC CAC CGG CAG GAT GTG GAG TTT CCC GAG CAC

TTC CTG CAG CCG CTG GTG CCC CTG CCC TTT GCC GGC

TTC GTG GCG CAG GCG CCT AAC AAC TAC CGC CGC TTC

CTG GAG CTC AAG TTC GGG CCC GGG GTC ATC GAG AAC

CCC CAG TAC CCC AAC CCG GCA CTG CTG AGT CTG ACG

GGA AGC GGC TGA
```

TABLE 1

| Complete Genomes | GenBank Accession Number |
|---|---|
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |

TABLE 1-continued

| Complete Genomes | GenBank Accession Number |
|---|---|
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530802 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |

TABLE 1-continued

| Complete Genomes | GenBank Accession Number |
|---|---|
| Clade F | |
| Hu14 (AAV9) | AY530579 |
| Hu31 | AY530596 |
| Hu32 Clonal Isolate | AY530597 |
| AAV6 | Y18065, AF085716 |

TABLE 1-continued

| Complete Genomes | GenBank Accession Number |
|---|---|
| AAV 3 | NC_001729 |
| AAV 3B | NC_001863 |
| AAV4 | NC_001829 |
| Rh34 | AY243001 |
| Rh33 | AY243002 |
| Rh32 | AY243003 |

TABLE 2

Alignment between the native human FRKP coding sequence (SEQ ID NO: 2) and an optimized synthetic polynucleotide encoding FKRP (SEQ ID NO: 1)

```
(Nat) ATG CGG CTC ACC CGC TGC CAG GCT GCC CTG GCG GCC GCC ATC ACC CTC
(Opt) ATG AGA CTG ACA AGA TGC CAG GCC GCC CTG GCC GCT GCC ATC ACA CTG (Nat) AAC CTT CTG GTC CTC TTC TAT GTC TCG TGG CTG CAG CAC CAG CCT AGG
(Opt) AAT CTG CTG GTG CTG TTC TAT GTG TCC TGG CTG CAG CAC CAG CCC CGG (Nat) AAT TCC CGG GCC CGG GGG CCC CGT CGT GCC TCT GCT GCC GGC CCC CGT
(Opt) AAC TCT AGA GCC AGA GGC CCA AGA AGG GCC TCT GCC GCC GGA CCT AGA (Nat) GTC ACC GTC CTG GTG CGG GAG TTC GAG GCA TTT GAC AAC GCG GTG CCC
(Opt) GTG ACA GTG CTC GTG CGC GAG TTC GAG GCC TTC GAC AAT GCC GTG CCC (Nat) GAG CTG GTA GAC TCC TTC CTG CAG CAA GAC CCA GCC CAG CCC GTG GTG
(Opt) GAG CTG GTG GAC AGC TTC CTG CAG CAA GAC CCT GCT CAG CCT GTG GTG (Nat) GTG GCA GCC GAC ACG CTC CCC TAC CCG CCC CTG GCC CTG CCC CGC ATC
(Opt) GTG GCC GCC GAT ACA CTG CCT TAT CCT CCA CTG GCC CTG CCC AGA ATC (Nat) CCC AAC GTG CGT CTG GCG CTG CTC CAG CCC GCC CTG GAC CGG CCA GCC
(Opt) CCC AAT GTG CGA CTG GCT CTG CTG CAG CCC GCC CTG GAT AGA CCT GCC (Nat) GCA GCC TCG CGC CCG GAG ACC TAC GTG GCC ACC GAG TTT GTG GCC CTA
(Opt) GCC GCT AGC AGA CCT GAG ACA TAC GTG GCC ACC GAG TTC GTG GCC CTG (Nat) GTA CCT GAT GGG GCG CGG GCT GAG GCA CCT GGC CTG CTG GAG CGC
(Opt) GTG CCT GAT GGC GCC AGA GCT GAA GCT CCC GCG CTG CTG GAA AGA (Nat) ATG GTG GAG GCG CTC CGC GCA GGA AGC GCA CGT CTG GTG GCC GCC
(Opt) ATG GTG GAA GCC CTG AGA GCC GGC AGC GCC AGA CTG GTG GCT GCT (Nat) CCG GTT GCC ACG GCC AAC CCT GCC AGG TGC CTG GCC CTG AAC GTC AGC
(Opt) CCT GTG GCT ACC GCC AAC CCT GCC AGA TGT CTG GCC CTG AAT GTG TCC (Nat) CTG CGA GAG TGG ACC GCC CGC TAT GGC GCA GCC CCC GCC GCG CCC
(Opt) CTG AGA GAG TGG ACC GCC AGA TAC GGC GCT GCC CCT GCC GCT CCT (Nat) CGC TGC GAC GCC CTG GAC GGA GAT GCT GTG GTG CTC CTG CGC GCC CGC
(Opt) AGA TGT GAT GCT CTG GAT GGC GAC GCC GTG GTG CTG CTG AGA GCC AGG (Nat) GAC CTC TTC AAC CTC TCG GCG CCC CTG GCC CGG CCG GTG GGC AAC AGC
(Opt) GAC CTG TTC AAC CTG AGC GCC CCT CTG GCC AGA CCT GTG GGC ACA AGC (Nat) CTC TTT CTG CAG ACC GCC CTT CGC GGC TGG GCG GTG CAG CTG CTG GAC
(Opt) CTG TTT CTG CAG ACA GCC CTG AGG GGC TGG GCC GTG CAG CTG CTG GAT (Nat) TTG ACC TTC GCC GCG GCG CGC CAG CCC CCG CTG GCC ACG GCC CAC
(Opt) CTG ACA TTT GCC GCT GCC AGA CAG CCT CCT CTG GCC ACA GCC CAT (Nat) GCG CGC TGG AAG GCT GAG CGC GAG GGA CGC GCT CGG CGC GCG GCG
(Opt) GCC AGA TGG AAG GCC GAG AGA GAG GGC AGA GCC AGA AGG GCT GCT
```

TABLE 2-continued

Alignment between the native human FRKP coding sequence (SEQ ID NO: 2) and an optimized synthetic polynucleotide encoding FKRP (SEQ ID NO: 1)

```
(Nat) CTG CTC CGC GCG CTG GGC ATC CGC CTA GTG AGC TGG GAA GGC GGG CGG
(Opt) CTG CTG AGG GCC CTG GGC ATC AGA CTG GTG TCT TGG GAA GGC GGC AGA (Nat) CTG GAG TGG TTC GGC TGC AAC AAG GAG ACC ACG CGC TGC TTC GGA ACC
(Opt) CTC GAG TGG TTC GGC TGC AAC AAA GAA ACC ACC CGG TGC TTC GGC ACC (Nat) GTG GTG GGC GAC ACG CCC GCC TAC CTC TAC GAG GAG CGC TGG ACG CCC
(Opt) GTC GTG GGC GAT ACA CCA GCC TAC CTG TAC GAG GAA AGA TGG ACC CCC (Nat) CCC TGC TGC CTG CGC GCG CTG CGC GAG ACC GCC CGC TAT GTG GTG GGC
(Opt) CCT TGC TGC CTG CGG GCC CTG AGA GAA ACA GCC AGA TAT GTC GTG GGC (Nat) GTG CTG GAG GCT GCG GGC GTG CGC TAC TGG CTC GAG GGC GGC TCA
(Opt) GTG CTG GAA GCC GCT GGC GTG CGA TAT TGG CTG GAA GGC GGA TCT (Nat) CTG CTG GGG GCC GCC CGC CAC GGG GAC ATC ATC CCA TGG GAC TAC GAC
(Opt) CTG CTG GGA GCC GCC AGG CAC GGC GAC ATC ATC CCT TGG GAC TAC GAC (Nat) GTG GAC CTG GGC ATC TAC TTG GAG GAC GTG GGC AAC TGC GAG CAG CTG
(Opt) GTG GAC CTG GGC ATC TAC CTG GAA GAT GTG GGC AAC TGC GAG CAG CTG (Nat) CGG GGG GCA GAG GCC GGC TCG GTG GTG GAT GAG CGC GGC TTC GTA
(Opt) AGA GGC GCC GAA GCC GGC TCT GTG GTG GAT GAG AGC GGC TTC GTG (Nat) TGG GAG AAG GCG GTC GAG GGC GAC TTT TTC CGC GTG CAG TAC AGC GAA
(Opt) TGG GAG AAG GCC GTG GAA GGC GAC TTC TTC CGG GTG CAG TAC AGC GAG (Nat) AGC AAC CAC TTG CAC GTG GAC CTG TGG CCC TTC TAC CCC CGC AAT GGC
(Opt) AGC AAC CAT CTG CAT GTG GAC CTG TGG CCC TTC TAC CCC CGG AAC GGC (Nat) GTC ATG ACC AAG GAC ACG TGG CTG GAC CAC CGG CAG GAT GTG GAG TTT
(Opt) GTG ATG ACC AAG GAC ACC TGG CTG GAC CAC CGG CAG GAC GTG GAA TTC (Nat) CCC GAG CAC TTC CTG CAG CCG CTG GTG CCC CTG CCC TTT GCC GGC TTC
(Opt) CCC GAG CAC TTT CTG CAG CCC CTG GTG CCA CTG CCT TTC GCC GGA TTT (Nat) GTG GCG CAG GCG CCT AAC AAC TAC CGC CGC TTC CTG GAG CTC AAG TTC
(Opt) GTG GCC CAG GCC CCC AAC AAC TAC CGG CGG TTC CTG GAA CTG AAG TTC (Nat) GGG CCC GGG GTC ATC GAG AAC CCC CAG TAC CCC AAC CCG GCA CTG CTG
(Opt) GGC CCT GGC GTG ATC GAG AAC CCC CAG TAC CCT AAC CCT GCC CTG CTG (Nat) AGT CTG ACG GGA AGC GGC TGA (SEQ ID NO: 2)
(Opt) AGC CTG ACC GGC AGC GGC TAA (SEQ ID NO: 1)
```

What is claimed is:

1. A synthetic polynucleotide encoding a human fukutin-related protein (FKRP), wherein the synthetic polynucleotide comprises the nucleotide sequence as set forth in SEQ ID NO:1.

2. The synthetic polynucleotide of claim 1, wherein the nucleotide sequence as set forth in SEQ ID NO: 1 is operably linked to a promoter.

3. The synthetic polynucleotide of claim 2, wherein the promoter is a creatine kinase (CK) promoter, or a chicken β-actin promoter (CB).

4. The synthetic polynucleotide of claim 3, wherein the promoter comprises an enhancer sequence.

5. The synthetic polynucleotide of claim 4, wherein the enhancer sequence comprises a CMV enhancer, a muscle creatine kinase enhancer, and/or a myosin light chain enhancer.

6. A vector comprising the synthetic polynucleotide of claim 1.

7. The vector of claim 6, wherein the vector is a viral vector.

8. The vector of claim 7, wherein the viral vector is an adeno-associated virus (AAV) vector.

9. The vector of claim 8, wherein the AAV vector is an AAV type 1, AAV type 2, AAV type 3a, AAV type 3B, AAV type 4, AAV type 5, AAV type 6, AAV type 7, AAV type 8, AAV type 9, AAV type 10, AAV type 11, avian AAV, bovine AAV, canine AAV, equine AAV, or ovine AAV.

10. The vector of claim 6 further comprising a mir 122 binding element.

11. An isolated transformed cell comprising the synthetic polynucleotide of claim 1.

* * * * *

UNITED STATES PATENT AND TRADEMARK OFFICE
CERTIFICATE OF CORRECTION

PATENT NO. : 10,350,305 B2
APPLICATION NO. : 15/687196
DATED : July 16, 2019
INVENTOR(S) : Lu et al.

Page 1 of 1

It is certified that error appears in the above-identified patent and that said Letters Patent is hereby corrected as shown below:

In the Specification

Column 3, Line 32: Please correct "NICK" to read -- MCK --

Column 3, Line 48: Please correct "FKRPS29" to read -- FKRP829 --

Column 10, Line 6: Please correct "\Vu et al." to read -- Wu et al. --

Column 11, Line 61: Please correct "Muzvczka" to read -- Muzyczka --

Column 13, Line 25: Please correct "SEQ IF)" to read -- SEQ ID --

Column 26, Line 20: Please correct "P448l" to read -- P448L --

Column 31, Table 1, Line 12: Please correct "AAV6" to read -- AAV5 --

Signed and Sealed this
Twenty-ninth Day of October, 2019

Andrei Iancu
*Director of the United States Patent and Trademark Office*